(12) United States Patent
Damstrup et al.

(10) Patent No.: US 11,246,929 B2
(45) Date of Patent: Feb. 15, 2022

(54) COMBINATION OF A PROTEIN KINASE INHIBITOR AND AN ADDITIONAL CHEMOTHERAPEUTIC AGENT

(71) Applicant: Merck Patent GmbH, Darmstadt (DE)

(72) Inventors: Lars Damstrup, Hilleroed (DK); Thomas Grombacher, Reinheim (DE); Christian Sirrenberg, Darmstadt (DE); Lyubomir Vassilev, Bedford, MA (US); Astrid Zimmermann, Muehltal (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/462,309

(22) PCT Filed: Dec. 18, 2017

(86) PCT No.: PCT/EP2017/083272
§ 371 (c)(1),
(2) Date: May 20, 2019

(87) PCT Pub. No.: WO2018/114776
PCT Pub. Date: Jun. 28, 2018

(65) Prior Publication Data
US 2019/0365896 A1 Dec. 5, 2019

Related U.S. Application Data
(60) Provisional application No. 62/436,046, filed on Dec. 19, 2016.

(51) Int. Cl.
| | | |
|---|---|---|
| A61K 31/5377 | (2006.01) |
| A61K 31/357 | (2006.01) |
| A61K 33/243 | (2019.01) |
| A61P 35/00 | (2006.01) |
| A61K 41/00 | (2020.01) |
| A61K 9/00 | (2006.01) |

(52) U.S. Cl.
CPC ........ *A61K 41/0038* (2013.01); *A61K 9/0019* (2013.01); *A61K 31/357* (2013.01); *A61K 31/5377* (2013.01); *A61K 33/243* (2019.01); *A61P 35/00* (2018.01)

(58) Field of Classification Search
CPC combination set(s) only.
See application file for complete search history.

(56) References Cited

U.S. PATENT DOCUMENTS

2013/0281431 A1 10/2013 Charifson et al.
2016/0083401 A1 3/2016 Fuchss et al.

FOREIGN PATENT DOCUMENTS

WO 2009036082 A2 3/2009
WO 2009111691 A2 9/2009

OTHER PUBLICATIONS

Dietlein et al., "Cancer-specific defects in DNA repair pathways as targets for personalized therapeutic approaches", Trends in Genetics, vol. 30, No. 8, Aug. 2014, (pp. 324-339).
Dobbs et al., "A Structural model for regulation of NHEJ by DNA-PKcs autophosphorylation", DNA Repair, vol. 9, 2010, (pp. 1307-1314).
Goytisolo et al., "The Absence of the DNA-Dependent Protein Kinase Catalytic Subunit in Mice Results in Anaphase Bridges and in Inceased Telomeric Fusions with Normal Telomere Length and G-Strand Overhang", Mol. And Cell. Biology, Jun. 2001 (pp. 3642-3651).
Pastwa et al., "Wortmannin potentiates the combined effect of etoposide and cisplatin in human glioma cells," International Journal of Biochemistry and Cell Biology, vol. 53, Aug. 2014 (pp. 423-431).
Riabinska et al., "Therapeutic Targeting of a Robust Non-Oncogene Addiction to PRKDC in ATM-Defective Tumors", Sci Transl Med vol. 5, 2013 (pp. 1-11).
Salles et al, "The DNA repair complex DNA-PK, a pharmacological target in cancer chemotherapy and radiotherapy", Pathologie Biologie vol. 54, 2006, (pp. 185-193).
Sirrenberg et al., "Abstract 4183: A novel selective DNA-PK inhibitor, M3814, as a potential combination partner of Etoposide and Cisplatin in the therapy of lung cancer," AACR Annual.
Smith et al., "The DNA-dependent protein kinase", Genes & Development vol. 13, 1999, (pp. 916-934).
Williams et al., "The Telomere Dysfunction and DNA-PKcs Deficiency: Characterization and Consequence", Cancer Res. vol. 69 (5) Mar. 2009, (pp. 2100-2107).
Yilmaz et al., "Carboplatin plus etoposide for extensive stage small-cell lung cancer: an experience with AUC 6 doses of carboplatin," Indian Journal of Cancer, vol. 48, No. 4, Oct.-Dec. 2011 (pp. 454-459).
International Search Report and Written Opinion issued by the European Patent Office as International Searching Authority for International Application No. PCT/EP2017/083272, dated Mar. 12, 2018.

*Primary Examiner* — Samira J Jean-Louis
(74) *Attorney, Agent, or Firm* — Dechert LLP; Andrea L. C. Reid; Joseph W. Arico

(57) ABSTRACT

Combination therapy for the treatment of cancer.

11 Claims, 18 Drawing Sheets

Combination of Compound 1 with etoposide in NCI-H460 viability assay in vitro (compound incubation for 72h)

Combination of Compound 1 with cisplatin in NCI-H460 viability assay in vitro (compound incubation for 72h)

▼ Cisplatin (monotherapy)
▲ Cisplatin+1, 1µM Compound 1 (combination)
--- % Effect of 1, 1µM Compound 1 (monotherapy)

Combination of Compound 1 with Etoposide in MO59K (DNA-PK wild type) viability assay (compound incubation for 168h)

▼ Etoposide (monotherapy)
■ Etoposide+370nM Compound 1 (combination)
--- % Effect of 370nM Compound 1 (monotherapy)

Combination of Compound 1 with Etoposide in MO59J (DNA-PK deficient) viability assay (compound incubation for 168h)

▼ Etoposide (monotherapy)
■ Etoposide+333nM Compound 1 (combination)
--- % Effect of 333nM Compound 1 (monotherapy)

Antitumor Effect of Compound 1 in Combination with etoposide in the Lung and Colon Cancer Cell Line Panels in vitro

COMBINATION OF A PROTEIN KINASE INHIBITOR AND AN ADDITIONAL CHEMOTHERAPEUTIC AGENT

This present application is a National Stage Entry of international PCT Application, PCT/EP2017/083272, filed Dec. 18, 2017, which claims priority to U.S. Provisional Patent Application No. 62/436,046, filed on Dec. 19, 2016, the entire contents of each of which are incorporated by reference herein.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

DNA-dependent protein kinase (DNA-PK) is a serine/threonine protein kinase which is activated in conjunction with DNA. Biochemical and genetic data show that DNA-PK consists (a) of a catalytic sub-unit, which is called DNA-PKcs, and (b) two regulatory components (Ku70 and Ku80). In functional terms, DNA-PK is a crucial constituent on the one hand of the repair of DNA double-strand breaks (DSBs) and on the other hand of somatic or V(D)J recombination. In addition, DNA-PK and its components are connected with a multiplicity of further physiological processes, including modulation of the chromatin structure and telomeric maintenance (Smith & Jackson (1999) Genes and Dev 13: 916; Goytisolo et al. (2001) Mol. Cell. Biol. 21: 3642; Williams et al. (2009) Cancer Res. 69: 2100).

Human genetic material in the form of DNA is constantly subjected to attack by reactive oxygen species (ROSs), which are formed principally as by-products of oxidative metabolism. ROSs are capable of causing DNA damage in the form of single-strand breaks. Double-strand breaks can arise if prior single-strand breaks occur in close proximity. In addition, single- and double-strand breaks may be caused if the DNA replication fork encounters damaged base patterns. Furthermore, exogenous influences, such as ionising radiation (for example gamma or particle radiation), and certain anticancer medicaments (for example bleomycin) are capable of causing DNA double-strand breaks. DSBs may furthermore occur as intermediates of somatic recombination, a process which is important for the formation of a functional immune system of all vertebrates. If DNA double-strand breaks are not repaired or are repaired incorrectly, mutations and/or chromosome aberrations may occur, which may consequently result in cell death. In order to counter the severe dangers resulting from DNA double-strand breaks, eukaryotic cells have developed a number of mechanisms to repair them. Higher eukaryotes use predominantly so-called non-homologous end-joining, in which the DNA-dependent protein kinase adopts the key role. Biochemical investigations have shown that DNA-PK is activated most effectively by the occurrence of DNA-DSBs. Cell lines whose DNA-PK components have mutated and are non-functional prove to be radiation-sensitive (Smith and Jackson, 1999).

Many diseases are associated with abnormal cellular responses, proliferation and evasion of programmed cell-death, triggered by protein kinase-mediated events as described above and herein. While considerable progress in the development of protein kinase inhibitors that are useful as therapeutic agents has been made to date, there remains a need to identify which particular treatments and conditions may allow beneficial expansion of the protein kinase inhibitors' potential.

SUMMARY OF THE INVENTION

In some embodiments, the present invention provides methods of treating, stabilizing or lessening the severity or progression of one or more diseases or disorders associated with DNA-PK comprising administering to a patient in need thereof an inhibitor of DNA-PK in combination with an additional chemotherapeutic agent. In some aspects, the inhibitor of DNA-PK is (S)-[2-chloro-4-fluoro-5-(7-morpholin-4-yl-quinazolin-4-yl)-phenyl]-(6-methoxy-pyridazin-3-yl)-methanol, having the below structure Compound 1:

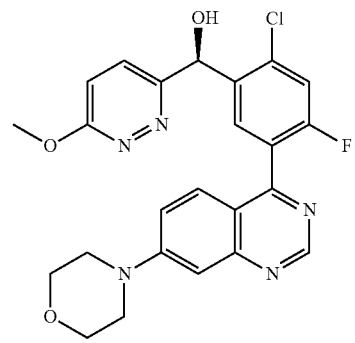

Compound 1 is described in detail in United States published patent application US 2016/0083401, published on Mar. 24, 2016 (referred to herein as "the '401 publication"), the entirety of which is hereby incorporated herein by reference. Compound 1 is designated as compound 136 in Table 4 of the '401 publication. Compound 1 is active in a variety of assays and therapeutic models demonstrating inhibition of DNA-PK (see, e.g., Table 4 of the '401 publication). Accordingly, Compound 1, or a pharmaceutically acceptable salt thereof, is useful for treating one or more disorders associated with activity of DNA-PK, as described in detail herein, infra.

The present invention, in particular, pertains to the following aspects and embodiments:

Firstly, it pertains to a method of treating a cancer in a patient in need thereof, comprising administering to said patient Compound 1, or a pharmaceutically acceptable salt thereof, in combination with at least one additional therapeutic agent selected from etoposide and a platin.

In preferred embodiments, the cancer is selected from cancer of the colon, lung, head and neck, pancreas, and histological subtypes thereof.

In some preferred embodiments, Compound 1 is administered with etoposide.

In alternative preferred embodiments, Compound 1 is administered with cisplatin.

In other preferred embodiments, Compound 1 is administered with both etoposide and cisplatin.

The method of treatment as set out above may further comprise a step of administering radiation therapy to the patient.

In any of the preferred embodiments, Compound 1 may be administered in an amount of about 1 to about 800 mg, for instance in an amount of about 10 to about 800 mg.

Etoposide may be administered intravenously in an amount of about 100 mg/m$^2$.

For instance, the etoposide may be administered via intravenous infusion over about 1 hour.

Cisplatin may be administered intravenously in an amount of about at 75 mg/m$^2$.

For instance, the cisplatin may be administered via intravenous infusion over about 1 hour.

In the method of treating cancer in a patient in need thereof, which comprises administering to said patient Compound 1, or a pharmaceutically acceptable salt thereof, in combination with etoposide, the effect of Compound 1 in combination with etoposide is synergistic wherein the etoposide induced myelo- and lymphoid reductions are not further increased by Compound 1.

Moreover, the present invention provides Compound 1 or a pharmaceutically acceptable salt thereof for use in the treatment of cancer in combination with at least one additional therapeutic agent selected from etoposide and a platin. Preferred embodiments are as set out above in connection with the method of treatment, and as set out below.

Hence, the present invention provides Compound 1 or a pharmaceutically acceptable salt thereof for use in the treatment of cancer comprising administering to said patient Compound 1, or a pharmaceutically acceptable salt thereof, in combination with at least one additional therapeutic agent selected from etoposide and a platin. Preferred embodiments are as set out above in connection with the method of treatment, and as set out below.

The present invention also provides a combination of Compound 1 or a pharmaceutically acceptable salt thereof with at least one additional therapeutic agent selected from etoposide and a platin for use in the treatment of cancer. Preferred embodiments are as set out above in connection with the method of treatment, and as set out below.

The present invention also provides etoposide for use in the treatment of cancer in a patient in need thereof, comprising administering to said patient Compound 1, or a pharmaceutically acceptable salt thereof, in combination with at least one additional therapeutic agent selected from etoposide and a platin. Preferred embodiments are as set out above in connection with the method of treatment. Preferred embodiments are as set out above in connection with the method of treatment, and as set out below.

The present invention also provides the use of a combination of Compound 1 or a pharmaceutically acceptable salt thereof and at least one additional therapeutic agent selected from etoposide and a platin in the manufacture of a medicament for the treatment of cancer in a patient. Preferred embodiments are as set out above in connection with the method of treatment. Preferred embodiments are as set out above in connection with the method of treatment, and as set out below.

Particularly preferred is a combination of Compound 1 or pharmaceutically acceptable salt thereof and etoposide, optionally further combined with a platin, such as cisplatin.

Cancers for which the combination respectively method of treatment according to the present invention is particularly beneficial are set out in the exemplary embodiments, which are also relevant outside and beyond the particular experimental conditions applied. The higher the synergy score, the greater the beneficial effect. Of course, since Compound 1 is an inhibitor of DNA-PK, no efficacy would be expected in DNA-PK deficient cancer cells/types, as confirmed by the experimental data shown herein.

Additional embodiments describing methods of utilizing a provided combination are described in detail herein, infra.

Without wishing to be bound by theory, the following can be derived from the examples presented further below: The experimental data shown herein demonstrate potentiation of etoposide by Compound 1 over a broad activity range. The broadening of the activity range in comparison to the single agent suggests that Compound 1 increases the specificity of etoposide action, thus widening its clinical applications. The experimental results further provide strong evidence for a synthetic-lethality mechanism arising from the combination of etoposide with Compound 1.

DETAILED DESCRIPTION OF CERTAIN EMBODIMENTS OF THE INVENTION

Figure 1:
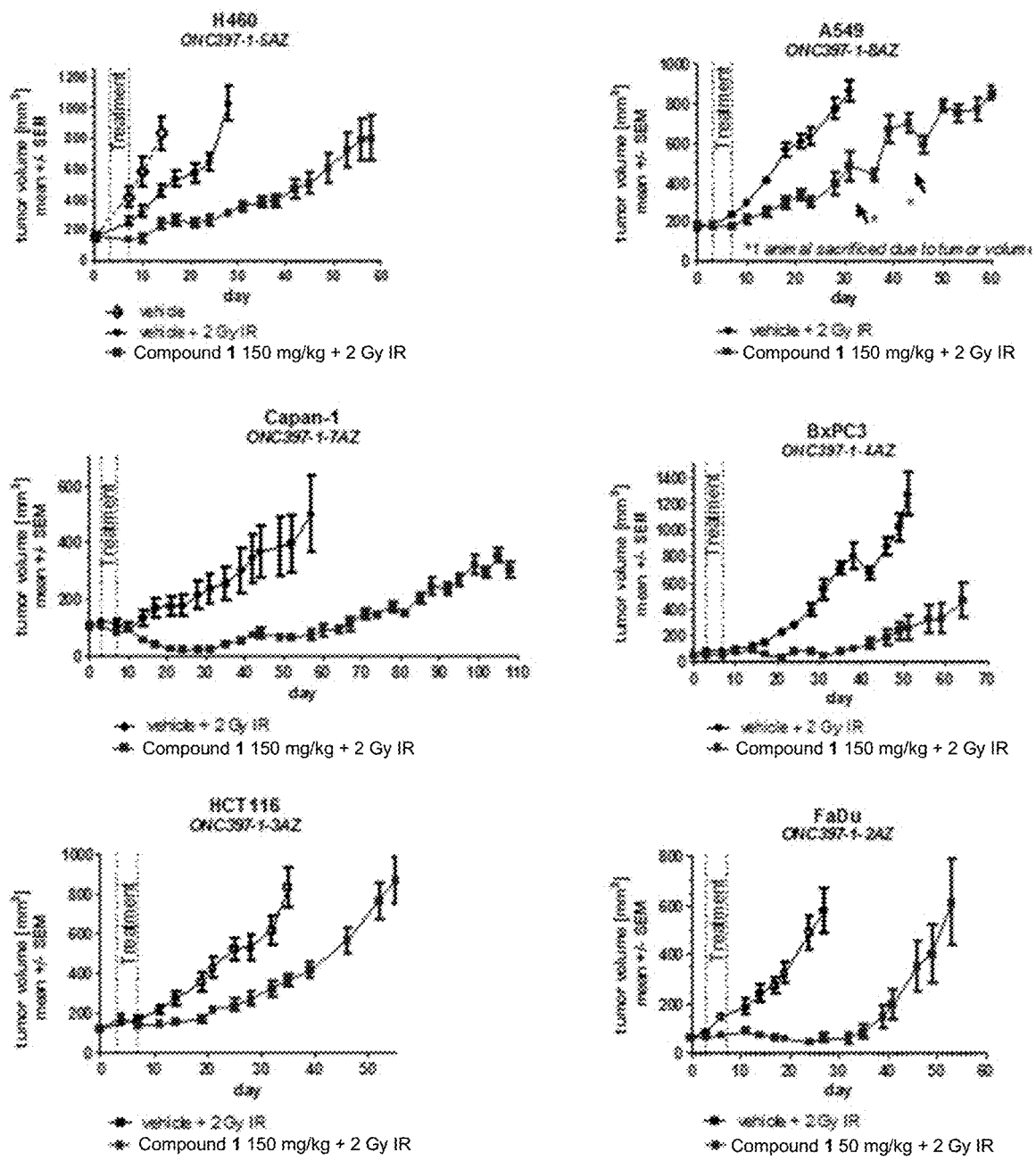
FIG. 1 shows the efficacy of Compound 1 in combination with radiation in six mouse xenograft models of human cancer.

As described herein, in some embodiments, the present invention provides methods of treating, stabilizing or lessening the severity or progression of one or more diseases or disorders associated with DNA-PK comprising administering to a patient in need thereof an inhibitor of DNA-PK in combination with an additional chemotherapeutic agent. As also described herein, in some embodiments, the present invention provides methods of treating cancer comprising administering to a patient in need thereof an inhibitor of DNA-PK in combination with an additional chemotherapeutic agent. In some embodiments, the DNA-PK inhibitor is Compound 1, or a pharmaceutically acceptable salt thereof.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

As used herein, the term "in combination" with regard to administration of Compound 1 and an additional chemotherapeutic agent means that each of Compound 1, or a pharmaceutically acceptable salt thereof, and the additional chemotherapeutic agent are administered to the patient in any order (i.e., simultaneously or sequentially) or together in a single composition, formulation, or unit dosage form. In some embodiments, the term "combination" means that the Compound 1, or pharmaceutically acceptable salt thereof, and the additional therapeutic agent, are administered simultaneously or sequentially. In certain embodiments, the Compound 1, or pharmaceutically acceptable salt thereof, and the additional therapeutic agent, are administered simultaneously in the same composition comprising the Compound 1, or pharmaceutically acceptable salt thereof, and the additional therapeutic agent. In certain embodiments, the Compound 1, or pharmaceutically acceptable salt thereof, and the additional therapeutic agent, are administered simultaneously in separate compositions (i.e., wherein the Compound 1, or pharmaceutically acceptable salt thereof, and the additional therapeutic agent are administered simultaneously each in a separate unit dosage form. It will be appreciated that Compound 1, or a pharmaceutically acceptable salt thereof, and the additional chemotherapeutic agent are administered on the same day or on different days and in any order as according to an appropriate dosing protocol.

The term "about" or "approximately" shall have the meaning of within 10%, for example within 5%, of a given value or range.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, condition, or disorder, to treat, diagnose, prevent, and/or delay the onset of the disease, condition, or disorder. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, condition, or disorder is the amount that alleviates, ameliorates, relieves, inhibits, prevents, delays onset of, reduces severity of and/or reduces incidence of one or more symptoms or features of the disease, condition, or disorder. In some embodiments, a "therapeutically effective amount" is at least a minimal amount of a compound, or composition containing a compound, which is sufficient for treating one or more symptoms of a disease or disorder associated with DNA-PK.

The terms "treat" or "treating," as used herein, refers to partially or completely alleviating, inhibiting, delaying onset of, preventing, ameliorating and/or relieving a disease or disorder, or one or more symptoms of the disease or disorder. As used herein, the terms "treatment," "treat," and "treating" refer to partially or completely alleviating, inhibiting, delaying onset of, preventing, ameliorating and/or relieving a disease or disorder, or one or more symptoms of the disease or disorder, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

The expression "unit dosage form" as used herein refers to a physically discrete unit of therapeutic formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

As described generally above, the present invention provides methods of treating, stabilizing or lessening the severity or progression of one or more diseases or disorders associated with DNA-PK comprising administering to a patient in need thereof an inhibitor of DNA-PK in combination with an additional chemotherapeutic agent. In some aspects, the inhibitor of DNA-PK is (S)-[2-chloro-4-fluoro-5-(7-morpholin-4-yl-quinazolin-4-yl)-phenyl]-(6-methoxy-pyridazin-3-yl)-methanol, having the below structure Compound 1:

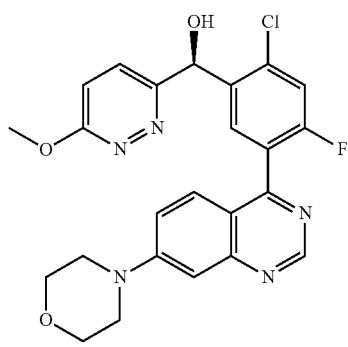

or a pharmaceutically acceptable salt thereof.

It is understood that although the methods described herein may refer to formulations, doses and dosing regimens/schedules of Compound 1, such formulations, doses and/or dosing regimens/schedules are equally applicable to any pharmaceutically acceptable salt of Compound 1. Accordingly, in some embodiments, a dose or dosing regimen for a pharmaceutically acceptable salt of Compound 1, or a pharmaceutically acceptable salt thereof, is selected from any of the doses or dosing regimens for Compound 1 as described herein.

Additional Chemotherapeutic Agents

As described generally above, provided methods comprise combination therapies utilizing Compound 1, or a pharmaceutically acceptable salt thereof, and a chemotherapeutic agent. In certain embodiments, the additional chemotherapeutic agent is etoposide. In certain embodiments, the additional chemotherapeutic agent is a platin. In certain embodiments, the additional chemotherapeutic agent is cisplatin. In certain embodiments, the additional chemotherapeutic agent is carboplatin. In some embodiments, the additional chemotherapeutic is a combination of both of etoposide and a platin. In some embodiments, the additional chemotherapeutic is a combination of both of etoposide and cisplatin. In some embodiments, the additional chemotherapeutic is a combination of both of etoposide and carboplatin.

Etoposide forms a ternary complex with DNA and the topoisomerase II enzyme which aids in DNA unwinding during replication. This prevents re-ligation of the DNA strands and causes DNA strands to break. Cancer cells rely on this enzyme more than healthy cells because they divide more rapidly. Therefore, etoposide treatment causes errors in DNA synthesis and promotes apoptosis of the cancer cells. Without wishing to be bound by any particular theory, it is believed that a DNA-PK inhibitor blocks one of the main pathways for repair of DSBs in DNA thus delaying the repair process and leading to an enhancement of the antitumor activity of etoposide.

Platins are platinum-based chemotherapeutic agents. As used herein, the term "platin" is used interchangeably with the term "platinating agent." Platinating agents are well known in the art. In some embodiments, the platin (or platinating agent) is selected from cisplatin, carboplatin, oxaliplatin, nedaplatin, and satraplatin.

Cisplatin crosslinks cellular DNA in several different ways interfering with cell division by mitosis. Most notable among the changes in DNA are the intrastrand cross-links with purine bases. These crosslinks are repaired primarily by nucleotide excision repair. The damaged DNA activates checkpoint mechanisms, which in turn activate apoptosis when repair proves impossible.

In certain embodiments, Compound 1, or a pharmaceutically acceptable salt thereof, is administered in combination with radiotherapy. In certain embodiments, provided methods comprise administration of Compound 1, or a pharmaceutically acceptable salt thereof, in combination with one or both of etoposide and cisplatin, wherein said method further comprises administering radiotherapy to the patient.

Methods of Treatment

Compound 1 is a potent and selective ATP-competitive inhibitor of DNA-PK, as demonstrated by crystallographic and enzyme kinetics studies. DNA-PK, together with five additional protein factors (Ku70, Ku80, XRCC4, Ligase IV, and Artemis) plays a critical role in the repair of DSB via NHEJ. Kinase activity of DNA-PK is essential for proper and timely DNA repair and the long-term survival of cancer cells (Salles et al., 2006; Dobbs et al., 2011). Without wishing to be bound by any particular theory, it is believed that the primary effects of Compound 1 are suppression of DNA-PK activity and DNA double strand break (DSB) repair, leading to altered repair of DNA and potentiation of antitumor activity of DNA-damaging agents.

In vitro data demonstrated a synergy of Compound 1 in combination with etoposide versus etoposide alone. Thus, in some embodiments, a provided combination of Compound I, or a pharmaceutically acceptable salt thereof, with etoposide is synergistic. In particular, the experimental results presented herein provide strong evidence for potentiation of etoposide, in particular, by Compound 1 or a pharmaceutically acceptable salt thereof.

In certain embodiments, the present invention provides a method of treating a cancer in a patient in need thereof comprising administering to said patient Compound 1, or a pharmaceutically acceptable salt thereof, in combination with at least one additional therapeutic agent selected from etoposide and a platin.

In certain embodiments, the present invention provides a method of treating a cancer selected from colon, lung, head and neck, pancreatic, and histological subtypes thereof (e.g., adeno, squamous, large cell) in a patient in need thereof comprising administering to said patient Compound 1, or a pharmaceutically acceptable salt thereof, in combination with at least one additional therapeutic agent selected from etoposide and a platin. In some embodiments, the platin (or platinating agent) is selected from cisplatin, carboplatin, oxaliplatin, nedaplatin, and satraplatin. In certain embodiments, the platin is cisplatin. In certain embodiments, the provided method further comprises administration of radiation therapy to the patient.

In certain embodiments, the present invention provides a method of treating a cancer selected from colon, lung, head and neck, pancreatic, and histological subtypes thereof (e.g., adeno, squamous, large cell) in a patient in need thereof comprising administering to said patient Compound 1, or a pharmaceutically acceptable salt thereof, in combination with etoposide and cisplatin. In certain embodiments, the provided method further comprises administration of radiation therapy to the patient.

Compound 1, or a pharmaceutically acceptable salt thereof, and compositions thereof according to methods of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like.

In some embodiments, the present invention provides a method of treating a cancer selected from colon, lung, head and neck, pancreatic, and histological subtypes thereof (e.g., adeno, squamous, large cell) in a patient in need thereof comprising administering to said patient Compound 1, or a pharmaceutically acceptable salt thereof, in an amount of about 1 to about 800 mg in combination with at least one additional therapeutic agent selected from a platin and etoposide.

In some embodiments, the present invention provides a method of treating a cancer selected from colon, lung, head and neck, pancreatic, and histological subtypes thereof (e.g., adeno, squamous, large cell) in a patient in need thereof comprising administering to said patient Compound 1, or a pharmaceutically acceptable salt thereof, in an amount of about 10 to about 800 mg in combination with at least one additional therapeutic agent selected from a platin and etoposide, in amounts according to the local clinical standard of care guidelines. In certain embodiments, cisplatin is administered intravenously in an amount of about 50 to about 75 mg/m$^2$. In some embodiments, etoposide is administered intravenously in an amount of about 50 to about 100 mg/m$^2$. Most commonly, cisplatin is administered at 75 mg/m$^2$ and etoposide at 100 mg/m$^2$.

In certain embodiments, the present invention provides a method of treating a cancer selected from colon, lung, head and neck, pancreatic, and histological subtypes thereof (e.g., adeno, squamous, large cell) in a patient in need thereof comprising administering to said patient Compound 1, or a pharmaceutically acceptable salt thereof, in combination with at least one additional therapeutic agent selected from etoposide and cisplatin, wherein the Compound 1, or a pharmaceutically acceptable salt thereof, and the additional therapeutic agent are provided in the same composition. In certain embodiments, the provided method further comprises administration of radiation therapy to the patient.

In certain embodiments, the present invention provides a method of treating a cancer selected from colon, lung, head and neck, pancreatic, and histological subtypes thereof (e.g., adeno, squamous, large cell) in a patient in need thereof comprising administering to said patient Compound 1, or a pharmaceutically acceptable salt thereof, in combination with at least one additional therapeutic agent selected from etoposide and cisplatin, wherein the Compound 1, or a pharmaceutically acceptable salt thereof, and the additional therapeutic agent are provided separate compositions for simultaneous or sequential administration to said patient. In certain embodiments, the provided method further comprises administration of radiation therapy to the patient.

In some embodiments, the present invention provides a method of treating a cancer in a patient in need thereof comprising administering to said patient Compound 1, or a pharmaceutically acceptable salt thereof, followed by administration of cisplatin and then administration of etoposide. In certain embodiments, Compound 1 is administered about 1-2, preferably about 1.5 hours prior to administration of the cisplatin. In some embodiments, Compound 1 is administered to said patient QD. In certain embodiments, Compound 1 is administered for 5 days. In some embodiments, Compound 1 is administered from about 4 days to about 3 weeks, for about 5 days, for about 1 week, or for about 2 weeks.

In certain embodiments, the cisplatin is administered via intravenous infusion. In certain embodiments, the cisplatin is administered via intravenous infusion at about 75 mg/m$^2$ over a 60-minute period. In some embodiments, the etoposide is administered via intravenous infusion. In certain embodiments, the etoposide is administered via intravenous infusion at about 100 mg/m$^2$ over a 60-minute period.

In certain embodiments, the etoposide is administered via intravenous infusion on Day 1 and then via intravenous infusion or oral administration on Days 2 and 3.

In some embodiments, provided methods comprise administering a pharmaceutically acceptable composition comprising Compound 1, or a pharmaceutically acceptable salt thereof, one, two, three, or four times a day.

In some embodiments, a pharmaceutically acceptable composition comprising Compound 1, or a pharmaceutically acceptable salt thereof, is administered daily.

In some embodiments, a pharmaceutically acceptable composition comprising Compound 1, or a pharmaceutically acceptable salt thereof, is administered once daily ("QD").

In some embodiments, a pharmaceutically acceptable composition comprising Compound 1, or a pharmaceutically acceptable salt thereof, is administered twice daily. In some embodiments, twice daily administration refers to a compound or composition that is administered "BID", or two equivalent doses administered at two different times in one day.

In some embodiments, a pharmaceutically acceptable composition comprising Compound 1, or a pharmaceutically acceptable salt thereof, is administered three times a day. In some embodiments, a pharmaceutically acceptable composition comprising Compound 1, or a pharmaceutically acceptable salt thereof, is administered "TID", or three equivalent doses administered at three different times in one day.

In some embodiments, a pharmaceutically acceptable composition comprising Compound 1, or a pharmaceutically acceptable salt thereof, is administered four times a day. In some embodiments, a pharmaceutically acceptable composition comprising Compound 1, or a pharmaceutically acceptable salt thereof, is administered "QID", or four equivalent doses administered at four different times in one day.

In some embodiments, Compound 1, or a pharmaceutically acceptable salt thereof, is administered to a patient under fasted conditions and the total daily dose is any of those contemplated above and herein.

In some embodiments, Compound 1, or a pharmaceutically acceptable salt thereof, is administered to a patient under fed conditions and the total daily dose is any of those contemplated above and herein.

In some embodiments, Compound 1, or a pharmaceutically acceptable salt thereof, is administered orally.

In a preferred embodiment of administering etoposide and Compound 1, or a pharmaceutically acceptable salt thereof, Compound 1 is administered on the same day and from, for example, about 2 hours before etoposide, or at about the same time as etoposide, or less than 7 hours after etoposide, for instance less than 5, 3 or 1 hour after etoposide.

Administration of Additional Chemotherapeutic Agent

In some embodiments, provided methods comprise administering a pharmaceutically acceptable composition comprising a chemotherapeutic agent one, two, three, or four times a day.

In some embodiments, a pharmaceutically acceptable composition comprising a chemotherapeutic agent is administered once daily ("QD").

In some embodiments, a pharmaceutically acceptable composition comprising a chemotherapeutic agent is administered twice daily. In some embodiments, twice daily administration refers to a compound or composition that is administered "BID", or two equivalent doses administered at two different times in one day.

In some embodiments, a pharmaceutically acceptable composition comprising a chemotherapeutic agent is administered three times a day. In some embodiments, a pharmaceutically acceptable composition comprising a chemotherapeutic agent is administered "TID", or three equivalent doses administered at three different times in one day.

In some embodiments, a pharmaceutically acceptable composition comprising a chemotherapeutic agent is administered four times a day. In some embodiments, a pharmaceutically acceptable composition comprising a chemotherapeutic agent is administered "QID", or four equivalent doses administered at four different times in one day. In some embodiments, a pharmaceutically acceptable composition comprising a chemotherapeutic agent is administered for a various number of days (for example 14, 21, 28) with a various number of days between treatment (0, 14, 21, 28).

In some embodiments, a chemotherapeutic agent is administered to a patient under fasted conditions and the total daily dose is any of those contemplated above and herein.

In some embodiments, a chemotherapeutic agent is administered to a patient under fed conditions and the total daily dose is any of those contemplated above and herein.

In some embodiments, a chemotherapeutic agent is administered orally for reasons of convenience. In some embodiments, when administered orally, a chemotherapeutic agent is administered with a meal and water. In another embodiment, the chemotherapeutic agent is dispersed in water or juice (e.g., apple juice or orange juice) and administered orally as a suspension. In some embodiments, when administered orally, a chemotherapeutic agent is administered in a fasted state.

A chemotherapeutic agent can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition. Pharmaceutically Acceptable Compositions of Compound 1 and/or a chemotherapeutic agent In some embodiments, the present invention provides a pharmaceutically acceptable composition comprising Compound 1, or a pharmaceutically acceptable salt thereof. In some embodiments, the present invention provides a pharmaceutically acceptable composition of a chemotherapeutic agent. In some embodiments, a composition comprising Compound 1, or a pharmaceutically acceptable salt thereof, is separate from a composition comprising a chemotherapeutic agent. In some embodiments, Compound 1, or a pharmaceutically acceptable salt thereof, and a chemotherapeutic agent are present in the same composition.

In certain embodiments, the present invention provides a composition comprising Compound 1, or a pharmaceutically acceptable salt thereof, and at least one of etoposide and cisplatin. In some embodiments, a provided composition comprising Compound 1, or a pharmaceutically acceptable salt thereof, and at least one of etoposide and cisplatin is formulated for oral administration.

Exemplary such pharmaceutically acceptable compositions are described further below and herein.

Liquid dosage forms for oral administration include, but are not limited to, pharmaceutically acceptable emulsions, microemulsions, solutions, suspensions, syrups and elixirs. In addition to Compound 1, or a pharmaceutically acceptable salt thereof, and/or a chemotherapeutic agent, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavouring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S. P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of Compound 1, and/or an additional chemotherapeutic agent, it is often desirable to slow absorption from subcutaneous or intramuscular injection. This may be accomplished by the use of a liquid suspension of crystalline or amorphous material with poor water solubility. The rate of absorption then depends upon its rate of dissolution that, in turn, may depend upon crystal size and crystalline form. Alternatively, delayed absorption of parenterally administered Compound 1, or a pharmaceutically acceptable salt thereof, and/or a chemotherapeutic agent, is accomplished by dissolving or suspending the compound in an oil vehicle. Injectable depot forms are made by forming microencapsule matrices of Compound 1, or a pharmaceutically acceptable salt thereof, and/or a chemotherapeutic agent, in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compound 1, or a pharmaceutically acceptable salt thereof, and/or a chemotherapeutic agent, can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms Compound 1, or a pharmaceutically acceptable salt thereof, and/or a chemotherapeutic agent, may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of Compound 1, or a pharmaceutically acceptable salt thereof, and/or a chemotherapeutic agent, include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

EXEMPLIFICATION

The following Examples illustrate the invention described above; they are not, however, intended to limit the scope of the invention in any way. The beneficial effects of the pharmaceutical compounds, combinations, and compositions of the present invention can also be determined by other test models known as such to the person skilled in the pertinent art.

Example 1

Efficacy of Compound 1 in Combination with Radiotherapy

The therapeutic relevance of DNA-PK inhibition by Compound 1 was investigated in vivo in combination with ionizing radiation (IR), a clinically established DSB-inducing treatment. Compound 1 was tested for activity in six xenograft mouse models of human cancer. The models were chosen from different cancer indications (colon, lung, head and neck, pancreatic), and histological subtypes (adeno, squamous, large cell). Ionizing radiation was administered using a fractionated schedule of 2 Gy per day administered over five consecutive days (total radiation dose=10 Gy). Compound 1 was given orally 10 min prior to each fraction of radiation (ONC397-1-2AZ, ONC397-1-3AZ, ONC397-1-4AZ, ONC397-1-5AZ, ONC397-1-8AZ).

In all models, oral administration of Compound 1 resulted in a strong enhancement of the radiation effect (FIG. 1—Efficacy of Compound 1 in Combination with Radiation in Six Mouse Xenograft Models of Human Cancer). Radiotherapy enhancing effect of Compound 1 was quantified across the tested models by the time to reaching 400% initial volume for the 150 mg/kg study arms. The resulting Kaplan-Meier plots were compared by the log-rank test. The enhancement ratio in this treatment setting was found to be between 1.5 (A549, HCT116), and 2.6 (NCI-H460) (Table 1).

TABLE 1

Summary of Log-Rank Test Results Using the Time to Reach 400% of Starting Tumor Volume (TV400%) from Xenograft Models Exposed to Radiation Alone or Radiation plus Compound 1

| Model | median time to $TV_{400\%}$ (days) IR only | median time to $TV_{400\%}$ (days) Combi | Enhancement Ratio$_{(combi\ IR\ only)}$ (95% CI) | P-value (log-rank test) | Study number for reference |
|---|---|---|---|---|---|
| NCI-H460 (lung, large cell) | 17 | 45 | 2.6 (2.2-3) | <0.0001 | ONC397-1-5AZ |
| A549 (lung, adeno) | 28.5 | 42 | 1.5 (1.1-1.9) | 0.0003 | ONC397-1-8AZ |
| BxPC3 (pancreas, adeno) | 36 | 73.5 | 2 (1.6-2.4) | <0.0001 | ONC397-1-4AZ |
| Capan-1 (pancreas, adeno) | 64.5 | 132 | 2 (1.7-2.3) | 0.027 | ONC397-1-7AZ |
| FaDu (H&N, squamous) | 21.5 | 46 | 2.1 (1.8-2.5) | <0.0001 | ONC397-1-2AZ |
| HCT116 (colon, adeno) | 30 | 46 | 1.5 (1.2-1.9) | 0.001 | ONC397-1-3AZ |

As demonstrated in the FaDu xenograft model, the results of which are summarized in Table 2, below, these effects were increased by applying either a higher dose of Compound 1 or a higher dose of radiation. For example, 100 mg/kg of Compound 1 in combination with a daily dose of 4 Gy (20 Gy total dose) led to a complete response (CR) in the FaDu model over the 92 day observation period (ONC397-1-11AZ), and when animals were irradiated with a daily dose of 6 Gy (30 Gy total dose) an enhancement ratio of 2 was observed with a 10 mg/kg Compound 1 dose (ONC397-1-12AZ).

Figure 3:
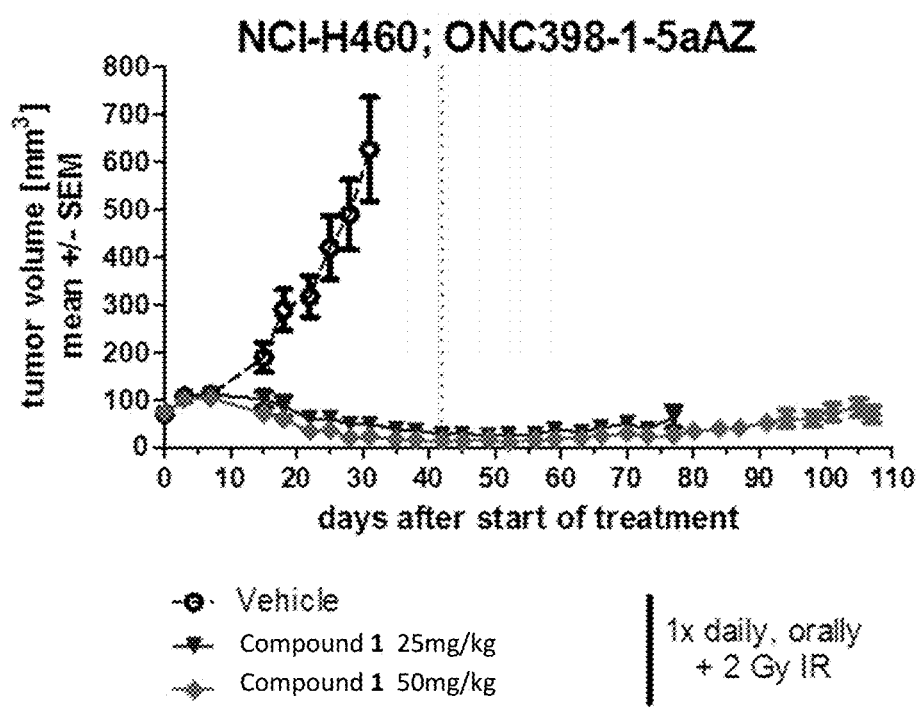
FIG. 3 shows the efficacy of Compound 1 in combination with IR in a 6-week treatment schedule in the NCI-H460 xenograft model.

The NCI-H460 was chosen as a model relatively insensitive to IR treatment. The tumors treated with IR only, rapidly progressed under treatment. However, the tumors treated with the IR and Compound 1 regressed during the treatment and observation period up to approximately day 90 (FIG. 3—Efficacy of Compound 1 in Combination with IR in a 6-week Treatment Schedule in the NCI-H460 xenograft model). The tumor xenografts in the mice treated with 50 mg/kg of the DNA-Pki did not exceed their starting volume until the end of the experiment at day 110 (42 days of treatment plus 68 days observation).

TABLE 2

Summary of Log-Rank Test Results Using TV400% from FaDu Xenograft Mode after Exposure to Different Doses of Radiation and Compound 1

| total IR dose (5 fractions in 1 week) | MSC dose (10 min prior to each IR fraction, po) | median time to $TV_{400\%}$ [days] IR only | median time to $TV_{400\%}$ [days] Combi | Enhancement Ratio$_{[combi/IR\ only]}$ (95% CI) | P-value (log-rank test) | Study Number for reference |
|---|---|---|---|---|---|---|
| 10 Gy | 25 mg/kg | 21.5 | 29.5 | 1.4 (1-1.8) | 0.02 | ONC397-1-2AZ |
|  | 100 mg/kg | 21.5 | 40 | 1.9 (1.4-2.3) | <0.0001 |  |
|  | 150 mg/kg | 21.5 | 46 | 2.1 (1.8-2.5) | <0.0001 |  |
|  | 300 mg/kg | 21.5 | >63 | 60% CR (d 63) | <0.0001 |  |
| 20 Gy | 5 mg/kg | 50 | 43 | 0.9 (0.5-1.2) | 0.3 | ONC397-1-11AZ |
|  | 10 mg/kg | 50 | 56.5 | 1.13 (0.8-1.5) | 0.75 |  |
|  | 100 mg/kg | 50 | >94 | 100% CR (d 94) | 0.004 |  |
| 30 Gy | 5 mg/kg | 50 | 69 | 1.4 (1-1.7) | 0.16 | ONC397-1-12AZ |
|  | 10 mg/kg | 50 | 94 | 1.9 (1.6-2.2) | 0.008 |  |
|  | 100 mg kg |  |  | not tolerated |  |  |

The standard radiotherapy regimen used in the clinic is a 6-week fractionated treatment schedule (5 fractions of 2 Gy IR per week—60 Gy total). To examine the therapeutic potential of Compound 1, this regiment was applied in two xenograft models of human cancer (FaDu and NCI-H460). Compound 1 was given orally 10 min prior to each fraction of radiation at doses of 5, 10, 25, and 50 mg/kg in the FaDu (refer to ONC397-1-13AZ) and 25 and 50 mg/kg in the NCI-H460 study (ONC398-1-5aAZ).

Figure 2:
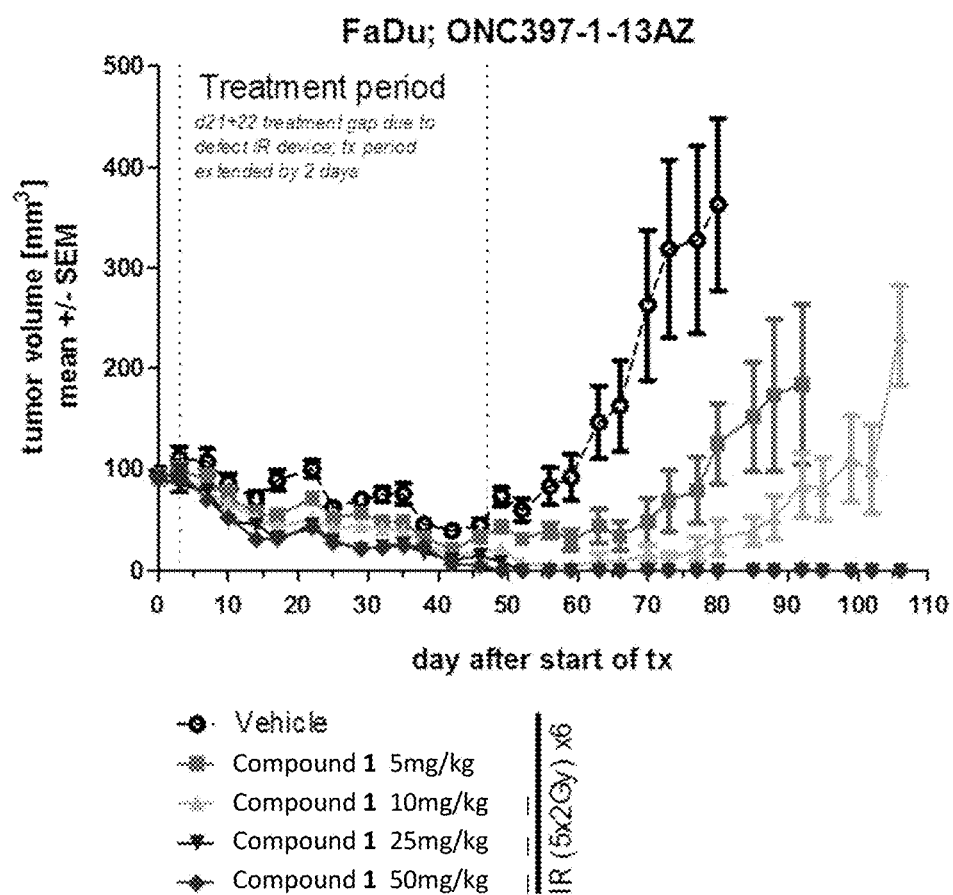
FIG. 2 shows the efficacy of Compound 1 in combination with IR in a 6-week treatment schedule in FaDu xenograft model.

In the FaDu study, this combination treatment resulted in a strong inhibition of tumor growth in comparison to tumors treated with IR alone. Complete tumor regression was observed in 44% of the animals treated with 10 mg/kg of Compound 1 and tumors did not regrow during the study period (113 days). At doses of 25 and 50 mg/kg, tumor xenograft regressed in all 10 animals and did not relapse until the end of the study (FIG. 2—Efficacy of Compound 1 in Combination with IR in a 6-week Treatment Schedule in FaDu Xenograft Model).

In both studies, the treatment was generally well tolerated. During the treatment period, the animals in all treatment groups showed moderate body weight loss, likely due to the daily treatment procedures—oral gavage, anesthesia, and IR over a period of 6 weeks. The body weight loss was fully reversible.

Example 2

Efficacy of Compound 1 in Combination with Etoposide and Cisplatin the Human NCI-H526 SCLC Xenograft Model For efficacy xenograft study 1014-1-58/BKU00105 female CD1 nu/nu mice [internal Batch ID 04108; Charles River Laboratories, Sulzfeld, Germany], aged 6-8 weeks, were used. For the hematology study 1015-1-3/BKU00106 immunocompetent female CD1 mice [internal Batch ID1406; Janvier Labs, Genest-Saint-Isle, France], aged 12 weeks were used. The mice were acclimatized to the housing conditions for 1 week. They were kept in groups of 10 in polysulfone cages Type III (42.5×26.6×15.5 cm; Techniplast, Hohenpeissenberg). Bedding consisted of aspen chips (E. Becker, Castrop-Rauxel). Room temperature was 24+/−2° C. and relative humidity was 50+/−10% at 15 air changes per hour. Drinking water (provided ad libitum) was supplemented with 1 mg/mL Chlorine and was adjusted to a pH of 6.5 with HCl. Sterile high protein maintenance diet for immunodeficient mice (Ssniff, Soest, product No V1244-72, γ-sterilized) was also provided ad libitum. The light cycle was set at 12 hrs light and 12 hrs darkness. Details of the study protocol are as follows:

For the efficacy xenograft study human small cell lung carcinoma cells 1014-1-58/BKU00105 NCI-H526 cells were obtained from the Merck KGaA central cell bank (cryo vial NCI-H526/5 17 Mar. 2011). The cells grown in suspension and were cultured in RPMI 1640 growth medium (Gibco No. 31870) incl 10% FCS (Biochrome Cat.: S0615, Lot 0707W), 2 mM L-Glutamine (Gibco No. 25030), 1 mM Sodium Pyruvate (Gibco No. 11360) at 37° C., 5% CO2 to obtain 2×108 cells in total. Cells were then washed 3× with DPBS and re-suspended in DPBS (—Mg/—Ca) with Matrigel (BD, Cat. no.: 354234) (1:1/v:v) to 2×107 cells/ml. Then the cell suspension (100 μL/animal) was subcutaneously inoculated in the right flank of immunodeficient CD1 mice.

Solutions

All reagents and buffers were stored according to the instructions of the manufacturers and used before the batch expiration date.

Compound 1 was produced at Merck KGaA Darmstadt, Germany. Formulation: The respective compound amount was weighed into a "Precellys"-tube [PEQ-Lab, 91-PCS-CK28R], lml vehicle (0.5% Methocel (K4M Premium USP/EP; Colorcon), 0.25% Tween20 (Merck, order no.: 8170721000) in Na-citrate buffer 300 mM pH 2.5) was added. The tube was placed in "precellys 24" tissue homogenizer [Bertin technologies, Montigny le Bretonneux (FR)] and ground twice at 6500 shakes for 30 sec. Afterwards, compound mixture was transferred to an appropriate glass vial and vehicle was added to bring the suspension to its final volume. Finally, the formulation (yellow colored, very fine suspension) was stirred for 10 min at 40° C. A fresh preparation was prepared once a week.

Etoposide VP-16 was obtained from Selleck Chemicals LLC, Cat No SI225-07. Etoposide was formulated as follows: 2 ml Chremophor was added to 12 mg Etoposide and sonicated to dissolve. 2 ml 100% Ethanol was added and mixed. Then 24 ml distilled water were added and sonicated. Final concentration of VP-16=0.4 mg/ml. A fresh preparation was prepared once a week.

Cisplatin was obtained from Metac GmbH, Infusions 50 mg/100 ml (0.5 mg/ml); delivery 2015/02/12, Lot.-No. M130845B. Cisplatin was diluted to the final application concentration using 0.9% saline (Braun, Reg.-ID.: 6726174.00.00). A fresh preparation was prepared once a week.

Treatment summary is set forth below:

| Group No. | Compound | Vehicle | Dose | Route | Schedule |
|---|---|---|---|---|---|
| | | N = 10 animals (female CD1 nude mice) per treatment group | | | |
| 1 | Vehicle | Methocel/Tween/Citrate buffer | — | po | daily |
| | | Cremophor/EtOH/H$_2$0 | | ip | 3 × weekly, 3 consecutive days |
| 2 | Compound 1 | Ref to 3.1.3 | 50 mg/kg | po | daily |
| 3 | Etoposide | Ref to 3.1.3 | 4 mg/kg | ip | 3 × weekly, 3 consecutive days |
| 4 | Etoposide | Ref to 3.1.3 | 4 mg/kg | ip | 3 × weekly, 3 consecutive days |
| | Cisplatin | | 3 mg/kg | ip | 1 × weekly |
| 5 | Compound 1 | 3.1.3 | 50 mg/kg | po | Daily* |
| | Etoposide | | 4 mg/kg | ip | 3 × weekly, 3 consecutive days |
| | Cisplatin | | 3 mg/kg | ip | 1 × weekly |
| | | | | | *(together with Etoposide when applicable) |
| 6 | Compound 1 | Ref to 3.1.3 | 50 mg/kg | po | Daily* |
| | Etoposide | | 4 mg/kg | ip | 3 × weekly, 3 consecutive days |
| | Cisplatin | | 3 mg/kg | ip | 1 × weekly |
| | | | | | *(7 h after Etoposide when applicable) |
| 7 | Compound 1 | Ref to 3.1.3 | 50 mg/kg | po | 4 × weekly (days where Etoposide is not given) |
| | Etoposide | | 4 mg/kg | ip | 3 × weekly, 3 consecutive days |
| | Cisplatin | | 3 mg/kg | ip | 1 × weekly |

Study Procedure

Tumor cell inoculation: The suspension of human NCI-H526 cells has been subcutaneously inoculated in the right flank of CD1 nu/nu mice in a volume of 100 μL DPBS (—Mg/—Ca) with Matrigel (1:1/v:v) and a concentration of 2×107 cells/ml.

Animal identification: All animals were individually identified using subcutaneously implanted electronic NONATEC transponders (LUTRONIC, Luxemburg). Implantation was performed on the back by hypodermic needle (18 gauge) after germ reduction of the skin with 70% alcohol. An electronic reader allowed the identification of each individual animal with the corresponding code number.

Tumor measurements and calculations: When the tumors reached a volume of 96-214 mm$^3$ the animals were randomized into 7 treatment groups with 10 animals each. Tumor length (L) and width (W) were measured twice weekly by calipers. The tumor volume was calculated using the formula L×W2/2. Data were collected in Study Advantage™ (data collection system).

Body weight: Body weight was monitored two/three times per week.

Treatment: dosing and scheduling per above. Compound 1 administered according to 3 different schedules:
1) Daily throughout the study and concomitant with SoC
2) Daily throughout the study, on days of SoC combination 7 h setup time between SoC treatment and Compound 1 application
3) Application only on days with no Etoposide treatment Blood sampling and processing for hematology: Blood was collected using a Sarstedt Microvette 500 K3E (Tri-Kalium-EDTA) REF20.1341, Lot. 4074501: Tubes were immediately put on a roller mixer (Stuart roller mixer SRT9D) and rolled until analysis. Hematological analysis was performed using the Analyser Sysmex xT-2000iV, located in A32/113.

Detection of Compound 1 and Etoposide in mouse plasma: Blood was collected as indicated in 11.3 (BKU00113) and 11.5 (BKU00105), respectively.

The quantitative determination of Compound 1 in mouse plasma was performed using HPLC-MS/MS assay in general compliance with procedures described the SO-ABC-6 Standard Operating Procedure 80.45.16.051 and the references provided therein.

Endpoints

T/C-value: The ability of a treatment to inhibit tumor growth was assessed at the end of each study by calculating the % T/C value according to following formulas:

% T/C delta>0 calculation (mean): [(end tumor volume treatment−start tumor volume treatment)/(end tumor volume control−start tumor volume control)]×100]

% T/C delta≤0 (regression) calculation (mean): [(end tumor volume treatment−start tumor volume treatment)/start tumor volume treatment]×100

Stasis: Stasis defined as tumors that demonstrated a smaller or larger size (≤−50% and ≤+25%) at the end of the experiment relative to that at the start of treatment Partial Regressions: Partial regression was defined as tumors that demonstrated a smaller size (≤50%) at the end of the experiment relative to that at the start of treatment.

Complete Regressions: Complete remissions were defined as tumors that were no longer palpable.

Tumor growth delay: The difference in days for treated versus control tumors to reach a specified volume, usually 1 $cm^3$ but could be less.

Toxicity: The bodyweight change in % denotes the difference between the weight at start of treatment and the end of treatment. Changes of bodyweight during the treatment course are particularly important as it is considered a measure for presence or absence of treatment-related toxicity. A dosage producing a 20% body weight change (mean of group) or ≥10% drug deaths was considered an excessively toxic dosage. Animal body weights included the tumor weights.

Blood Cell Counts

Statistical Analysis

The efficacy data have been analyzed by RM-ANCOVA and pairwise comparisons of the tumor volume data of the respective combination groups to tumor volume data of the SoC only treatment group.

The hematology data were evaluated by RM-ANOVA and Bonferroni multiple comparisons post test comparing the blood cell counts of the respective combination groups to the blood cell counts of the SoC only treatment group.

The therapeutic effect of Compound 1 in combination with the standard of care (SoC) regimen of etoposide and cisplatin was tested in the human small cell lung cancer xenograft model NCI-H526 in nude mice. Animals were treated with three 1-week cycles of chemotherapy consisting of Cisplatin (3 mg/kg once weekly) and Etoposide (4 mg/kg for three consecutive days per week). The combination with Compound 1 (50 mg/kg) was in three different schedules. 1) Compound 1 was applied daily throughout the study and concomitant with Etoposide on the respective days. 2) Compound 1 was applied daily throughout the study 7 h after Etoposide treatment on the respective days. 3) Compound 1 was separated from Etoposide treatment and only applied on days where no Etoposide was given. In the combination arm of the study Compound 1 was given in addition to chemotherapy (50 mg/kg daily throughout the study period, extending the three weeks of chemotherapy.

Figure 4:
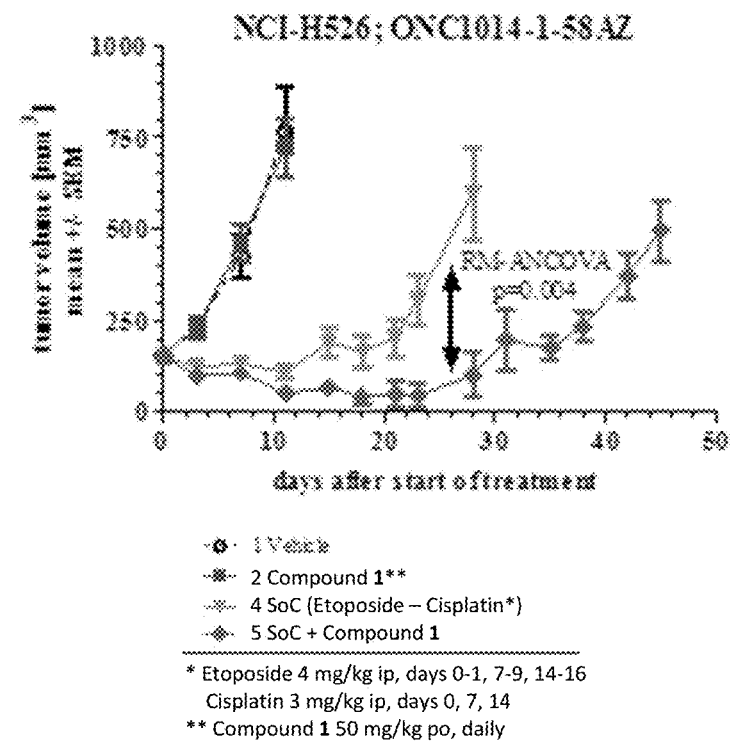
FIG. 4 shows the efficacy of Compound 1 in combination with etoposide/cisplatin in the NCI-H526 xenograft model.
Figure 4:
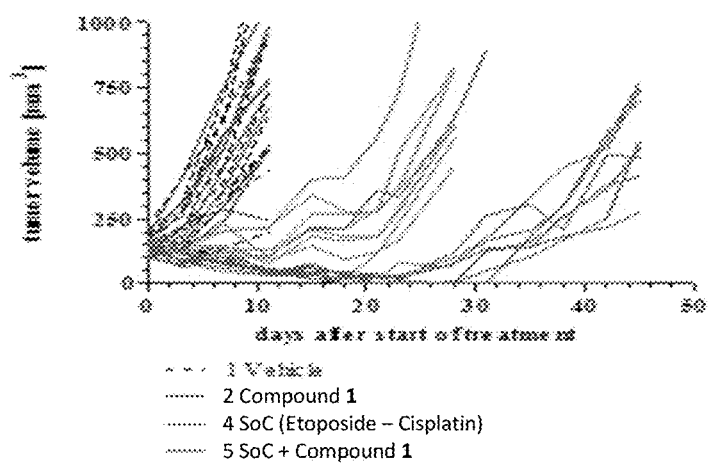
Figure 5:
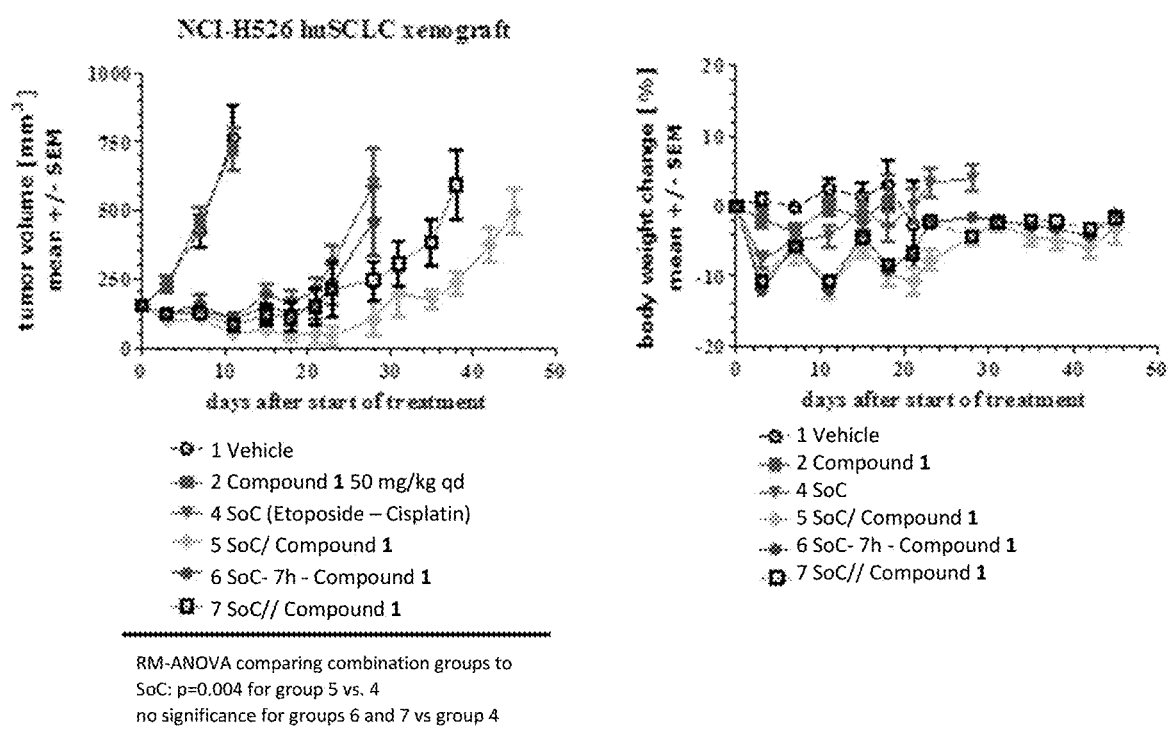
FIG. 5 shows that administering Compound 1 daily throughout the study resulted in better efficacy than separating SoC and Compound 1 treatment by either 7 h or days.

In combination with Etoposide and Cisplatin, Compound 1 shows significantly enhanced antitumor activity in the human SCLC NCI-H526 mouse xenograft model (FIG. 4—Efficacy of Compound 1 in Combination with etoposide/cisplatin in the NCI-H526 Xenograft Model (mean tumor volume left and individual tumor volumes right)) (refer to ONC1014-1-58AZ). The addition of Compound 1 to the SoC regimen of etoposide and cisplatin resulted in additional efficacy as compared to the SoC treatment arm. At the end of SoC treatment period (day 21) the mean tumor volume of the combination group (n=10) was 50 $mm^3$—a decrease of about 67% compared to starting volume, whereas the mean tumor volume of the SoC group (n=10) increased by 30% to about 200 $mm^3$. On day 28, 9/10 animals in the combination arm were progression free, 4/10 were showing complete response of which 3/10 stable disease and 1/10 regression. In the SoC arm 8/10 animals showed progressive disease. FIG. 5 shows that administering Compound 1 daily throughout the study resulted in better efficacy than separating SoC and Compound 1 treatment by either 7 h or days.

Figure 6:
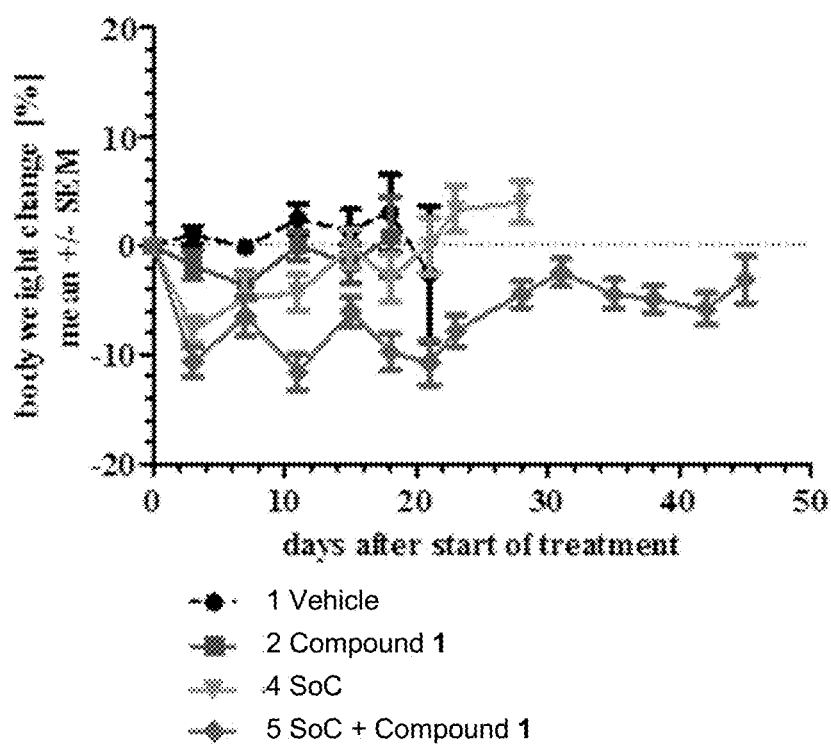
FIG. 6 shows the body weight change upon etoposide/cisplatin treatment and the combination with Compound 1 in mice.

SoC therapy induced body weight loss in the animals (FIG. 6—Body weight change upon etoposide/cisplatin treatment and the combination with Compound 1 in mice). Combining SoC with the Compound 1 led to additional body weight loss. All animals were supplemented with enabled food supply (DietGel® Boost mixed with water) throughout the study in order to keep body weight loss in a moderate range and stabilize their overall condition. After termination of SoC treatment at the end of chemotherapy cycle 3 (d21) the animals recovered despite the continuous Compound 1 administration.

Figure 7:
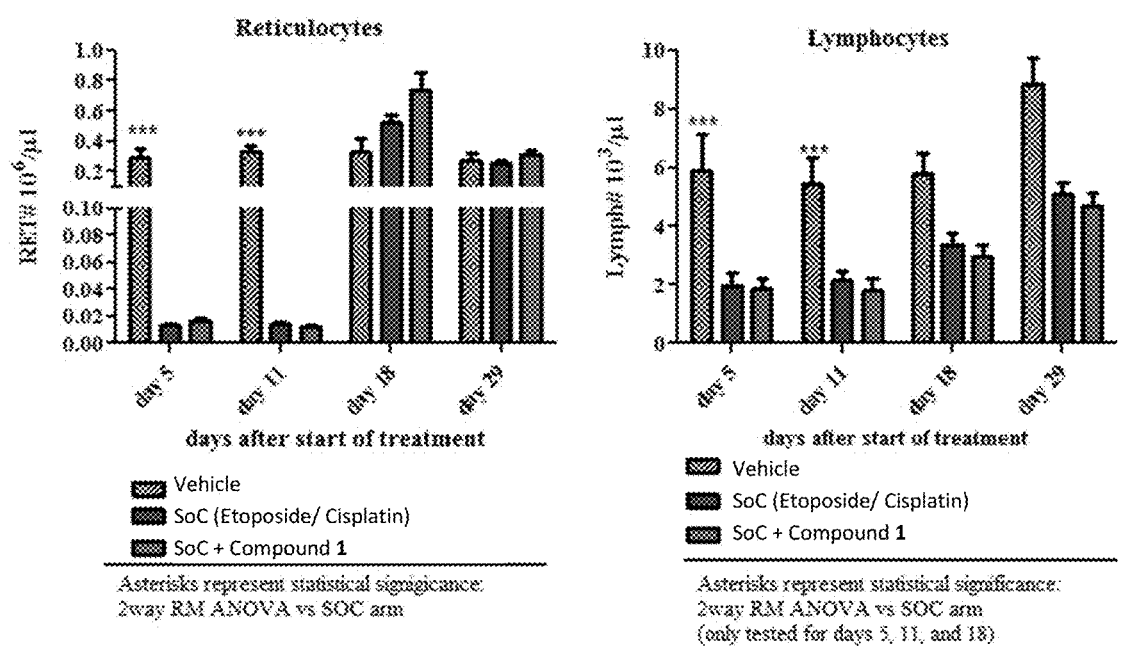
FIG. 7 shows the reticulocyte and lymphocyte counts under treatment with and recovery from etoposide/cisplatin and the combination with Compound 1.

In parallel with the antitumor effect of the etoposide/cisplatin/Compound 1 combination, the effect on myeloid and lymphoid cells was investigated in immunocompetent mice (refer to ONC1015-1-3AZ). Animals were treated at the same doses and schedules as in the antitumor study, but for two weeks only. Blood cell count was determined under treatment (days 5 and 11) and during recovery (days 18 and 24). FIG. 7—Reticulocyte and Lymphocyte counts under treatment with and recovery from etoposide/cisplatin and the combination with Compound 1 shows that reticulocytes and lymphocytes were significantly reduced upon treatment with etoposide and cisplatin. The addition of Compound 1 did not significantly affect blood cell reduction nor the recovery phase. Similar effects were seen for eosinophils and no significant effects were observed for neutrophils, and platelets. Since myeloid and lymphoid suppression is one of the dose limiting toxicities of the etoposide/cisplatin regimen in patients, the demonstrated absence of any significant additional toxicity is a positive outcome.

Example 3

Single Agent Compound 1 Treatment Inhibits LoVo Xenograft Growth

Figure 8:
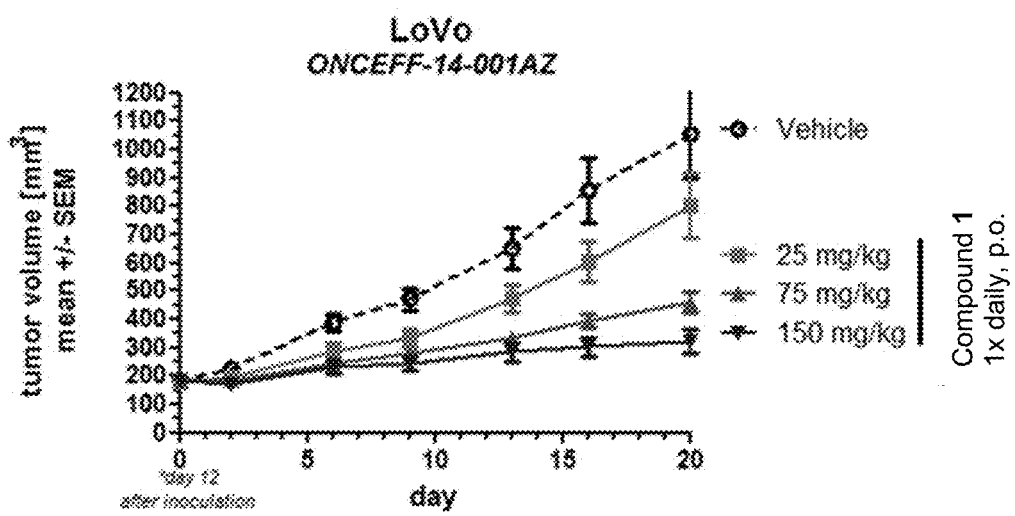
FIG. 8 shows the single agent efficacy of Compound 1 in the ATM pathway deficient LoVo xenograft model.

It has been reported recently that tumor cells with dysfunctional DNA repair pathway components can be addicted to DNA-PK, suggesting that DNA-PK inhibitors may have single agent activity in DNA repair deficient tumors (Riabinska et al., 2013, Dietlein et al., 2014). We tested the effect of Compound 1 on the growth of established LoVo colon carcinoma xenografts that are known to be deficient in ATM pathway function due to mutation in the MRE11 protein. Three week administration of the DNA-PK inhibitor to tumor bearing mice led to a dose-dependent tumor growth inhibition with nearly complete growth suppression at 150 mg/kg (FIG. 8—Single Agent Efficacy of Compound 1 in the ATM Pathway Deficient LoVo Xenograft Model) (refer to ONCEFF-14-001AZ).

Example 4

In Vivo Pharmacodynamic Effects of Compound 1

Figure 9:
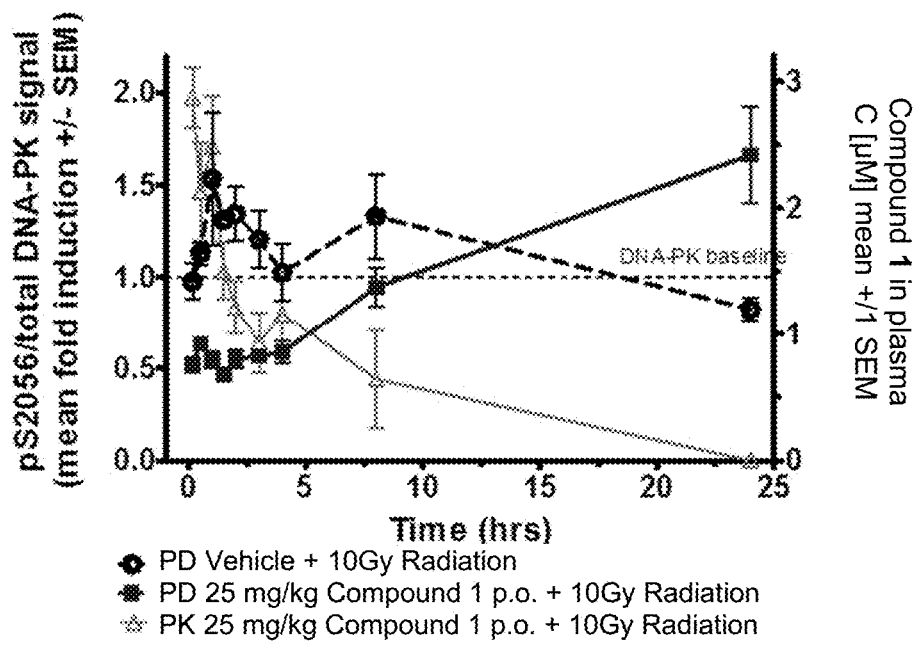
FIG. 9 shows that Compound 1 inhibits DNA-PK autophosphorylation (p-Ser2056) in WM164 xenograft tumor.

Following the induction of DSB by radiation therapy or other DNA damaging agents, the catalytic subunit of DNA-PK (DNA-PKc) is autophosphorylated at several serine and threonine residues. Ser2056 is one of the most prominent and best studied autophosphorylation sites. Because Ser2056 phosphorylation (p-Ser2056) correlated well with DNA-PK activation state it was chosen as the pharmacodynamics (PD) biomarker. Two different assay formats were established to measure p-Ser2056 in tumor tissue: ELISA and MSD format. In order to detect sequence reliable signal, IR was used at 50 Gy for the ELISA assay and 10 Gy for the more sensitive MSD assay. Dose-dependent inhibition of IR-induced DNA-PK phosphorylation (Ser2056) by Compound 1 was demonstrated in the human xenograft models FaDu and HCT116 by ELISA (refer to ONC101305BCS) and WM164 by the MSD assay. Mice with established WM164 tumors were given Compound 1 10 minutes prior to 10 Gy of IR and DNA-PK (p-Ser2056) levels in tumor tissue (PD) were measured at several time points and correlated with Compound 1 plasma concentration (PK). DNA-PK autophosphorylation was increased after IR showing a maximal stimulation between 1 and 2 hours. Co-administration of IR and Compound 1 (25 mg/kg) led to inhibition of DNA-PK autophosphorylation in tumor tissue with strongest effects corresponding to high plasma exposure of Compound 1. Inhibited level was below that in vehicle treated animals due to inhibition of the basal level of DNA-PK phosphorylation (p-Ser2056) (FIG. 9—Compound 1 Inhibits DNA-PK Autophosphorylation (p-Ser2056) in WM164 Xenograft Tumor) (refer to ONC20140508CS).

Example 5

Compound 1 in combination with etoposide or cisplatin was tested in the following cancer cell lines for inhibition of tumor cells: human lung carcinoma (NCI-H460), human glioblastoma (MO59K and MO59J), and human squamous cell carcinoma pharynx (FaDu). Details of the assay protocol and material utilized are set forth below.

Materials and Sources

| | |
|---|---|
| Nuncon surface 96-well plate (cell culture) | Nunc |
| DMEM | Pan Biotech GmbH |
| RPMI | Gibco |
| HAM F12 | Pan Biotech GmbH |
| Sodium Pyruvat | Gibco |
| L-Glutamin | Gibco |
| Non Essential Amino Acid | SIGMA |
| PBS (10x) Dulbecco | Gibco |
| 96-well microtiter plates (Polypropylene) | Nunc |
| AlamarBlue | Serotec |
| FCS (fetal bovine serum) | Biochrom |
| Trypsin/EDTA solution 10x | Biochrom AG |
| 75 cm culture flask | DB Falcon |
| Etoposide | SIGMA |
| Cisplatin | SIGMA |
| DMEM/F12 (1:1) | Gibco |
| Alamar blue | Serotec |
| NCI-H460 | Lung carcinoma human; ATCC HTB177 |
| MO59K | human glioblastoma: ATCC CRL-2365 |
| MO59J | human glioblastoma ATCC CRL-2366 |
| FaDu | human squamous cell carcinoma pharynx; ATCC HTB43 |

Instruments

| Instrument | Supplier |
|---|---|
| Incubator Heracell 150i | Heraeus |
| Flow | Herasafe |
| Tecan reader Connect | Tecan |
| HP D300 Digital Dispenser | HP//Tecan |

Test Article Concentrations

| Test material | Concentration in µM/nM | Duration | Vehicle |
|---|---|---|---|
| Compound 1 | 30 µM; 10 µM; 3.3 µM; 1.1 µM; 370 nM; 120 nM; 41 nM; 14 nM | 72 h | DMSO |
| Compound 1 | 30 µM; 10 µM; 3.3 µM; 1.1 µM; 370 nM; 120 nM; 41 nM; 14 nM | 168 h | DMSO |
| Etoposide | 10 µM; 3.3 µM; 1.1 µM; 370 nM; 120 nM; 41 nM; 14 nM; 4.7 nM | 72 h | DMSO |
| Etoposide | 10 µM; 3.3 µM; 1.1 µM; 370 nM; 120 nM; 41 nM; 14 nM; 4.7 nM | 168 h | DMSO |
| Etoposide | 10 µM; 2 µM; 400 nM; 80 nM; 16 nM; 3.2 nM; 0.64 nM; 0.13 nM | 168 h | DMSO |
| Cisplatin | 10 µM; 3.3 µM; 1.1 µM; 370 nM; 120 nM; 41 nM; 14 nM; 4.7 nM | 72 h | DMSO |

Cells were plated in a volume of 180 µl/well in 96-well plates: (FaDu: 1000 cells/well (168 h); NCI-H460 3000 cells/well (72 h) and 1000 cells/well (168 h); MO59J: 5000 cells/well (72 h) and 2000 cells/well (168 h); MO59K: 2000c/well (72 h) and 1000 cells/well (168 h)) and incubated at 37° C. and relevant C02 for 24 h hours. 20 µl per well of medium including serial dilutions of Compound 1 and/or Etoposide or Cisplatin were added to the culture plates and the incubation was continued further for 3 days (72 h) or 7 days (168 h) at 37° C. and relevant CO2. Compound 1 was pre-incubated for 30 min before Etoposide or Cisplatin were added.

Cells were plated in 200 µl volume per well (FaDu: 1000 cells/well (168 h); NCI-H460 3000 cells/well (72 h) and 1000 cells/well (168 h); MO59J: 5000 cells/well (72 h) and 2000 cells/well (168 h); MO59K: 2000c/well (72 h) and 1000 cells/well (168 h)). After 24 h incubation at 37° C. Compound 1, Etoposide or Cisplatin were dispensed by using the Digital HP Dispenser D300 (and the included dispensing software). Plates were further incubated for 3 days (72 h) or 7 days (168 h) at 37° C. and relevant CO2.

At the end of the compound incubation period 20 µl AlamarBlue reagent was added per well and the 96-well plates were incubated further up to seven hours. Absorption was determined at 540 nm by using Tecan Reader Connect and Magelan 7.

0% effect=cells treated with DMSO; −100% effect=no cells $$\% \text{ Effect} = \left[\frac{100*(\text{value cells with compound} - \text{value no cells})}{(\text{value cells no compound} - \text{value no cells})}\right] - 100$$

Results

Figure 10:
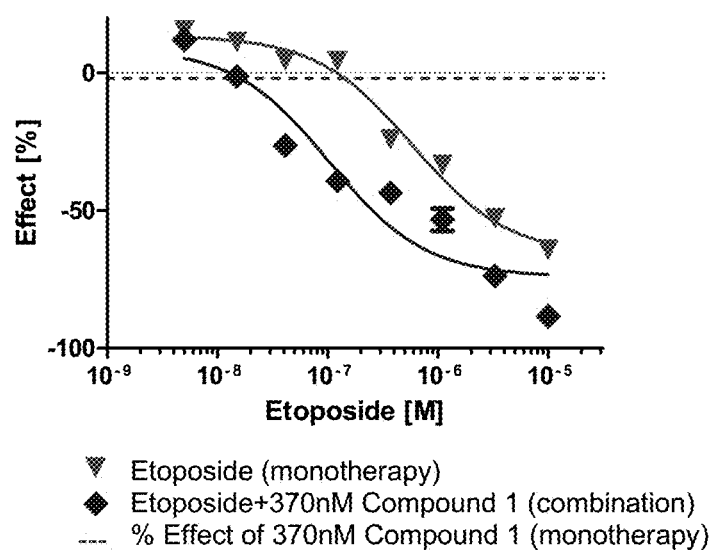
FIG. 10 shows the results of the combination of Compound 1 with Etoposide in NCI-H460 viability assay (compound incubation for 72 h).
Figure 12:
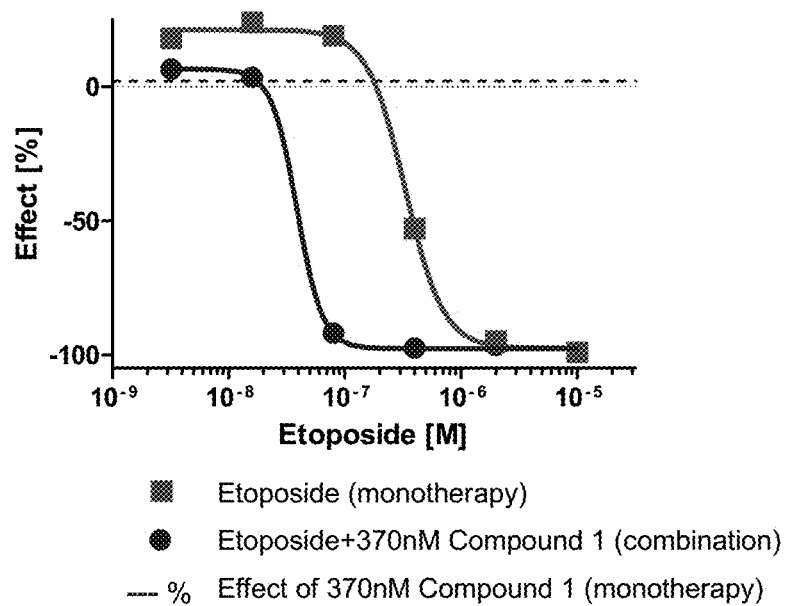
FIG. 12 shows the results of the combination of Compound 1 with Etoposide in MO59K (DNA-PK wild type) viability assay (compound incubation for 72 h).
Figure 13:
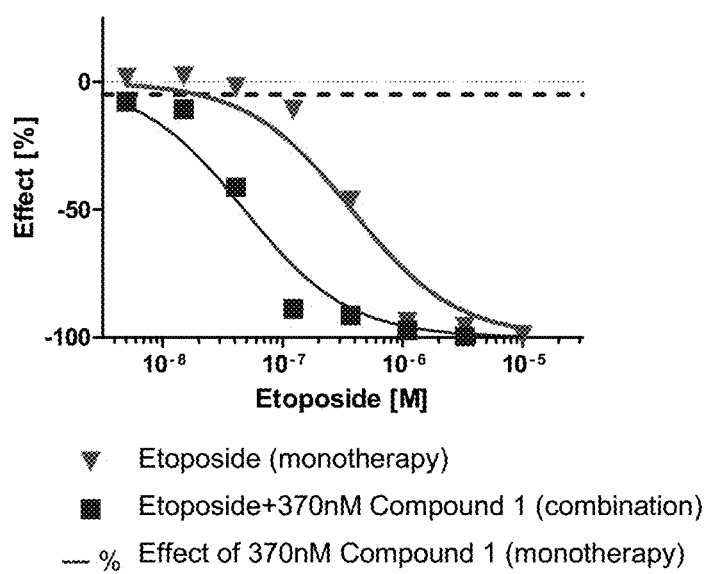
FIG. 13 shows the results of the combination of Compound 1 with Etoposide in MO59K (DNA-PK wild type) viability assay (compound incubation for 168 h).

Compound 1 showed enhanced inhibition of viability of NCI-H460, FaDu and MO59K (DNA-PK wild type) cells in vitro by using the combination with etoposide (FIGS. 10, 12 and 13).

Figure 18:
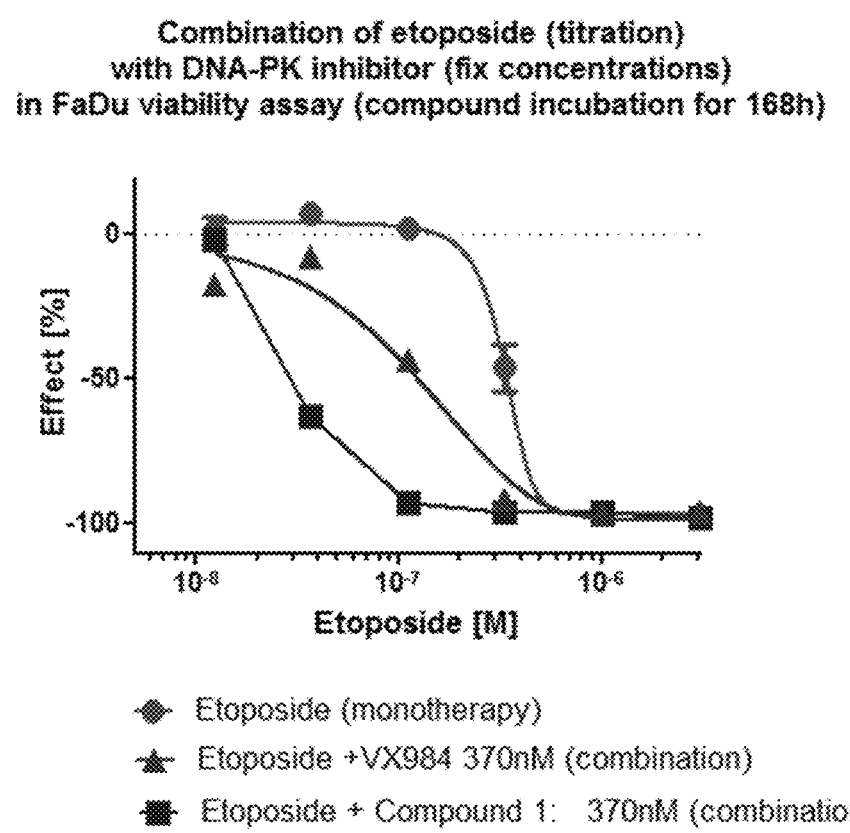
FIG. 18 shows the results of the combination of Compound 1 in comparison to VX-984 with Etoposide in MO59K (DNA-PK wild type) viability assay (compound incubation for 72 h).

Compound 1 compares favorably with another DNA-PK inhibitor, VX984, which requires higher concentrations of etoposide to arrive at the same % effect, as illustrated in FIG. 18. VX-984 represents the compound 8-[(1S)-2-[[6-(4,6-dideuterio-2-methylpyrimidin-5-yl)pyrimidin-4-yl]amino]-1-methylethyl]quinoline-4-carboxamide, as disclosed in WO 2013/163190, for instance.

Figure 11:
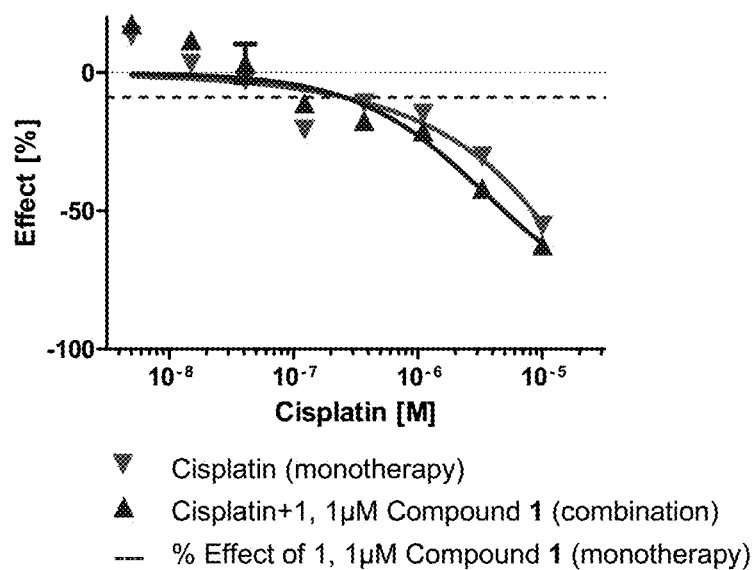
FIG. 11 shows the results of the combination of Compound 1 with Etoposide in NCI-H460 viability assay (compound incubation for 168 h).
Figure 14:
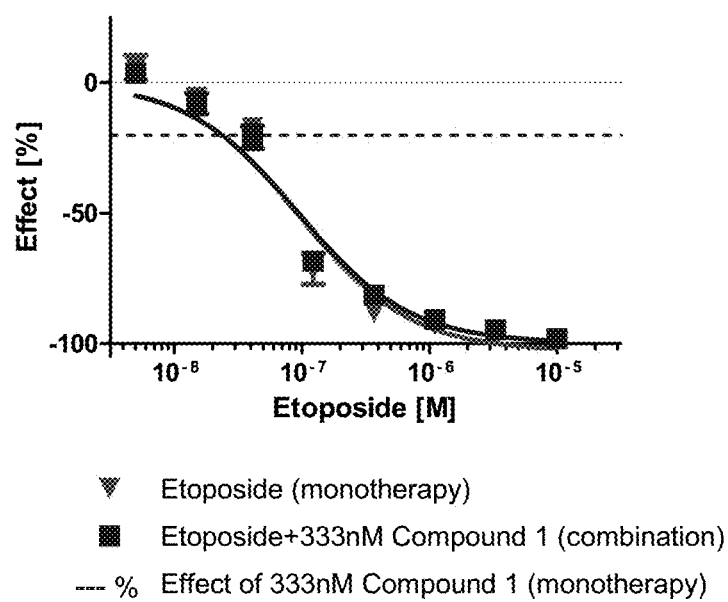
FIG. 14 shows the results of the combination of Compound 1 with Etoposide in MO59J (DNA-PK deficient) viability assay (compound incubation for 168 h).

MO59J cells, that are DNA-PK deficient (1), showed no such combination effect of Compound 1 with Etoposide under comparable conditions (FIG. 14). No significant combination effect of Compound 1 together with cisplatin on the viability of NCI-H460 was observed (FIG. 11).

Example 6

The effects on cell growth of etoposide treatment in combination with Compound 1 was analyzed in a panel of the following cell lines: A110L, A-427, A529L, A549, BEN, CACO2, CALU-1, Calu-3, CALU6, COLO205, COLO-677, COL0678, COLO-699, COR-L311, COR-L88, DLD1, DMS 114, DMS 153, DMS 454, DMS 53, DV-90, EBC-1, EPLC-272H, H-2171, H69V, HCC-15, HCC2935, HCC-366, HCC-44, HCC-827, HCT116, HCT15, HLC-1, HLF-a, H-MESO-1, HT29, IA-LM, IMR90, JU77, LC-2/ad, LK-2, L068, LOVO, LS123, LS411N, LU65, Lu99B, LUDLU-1, LXF-289, MIAPACA2, MS-1, MSTO-211H, NCI-H1048, NCI-H1105, NCI-H1299, NCI-H146, NCI-H1563, NCI-H1568, NCI-H1573, NCI-H1581, NCI-H1651, NCI-H1694, NCI-H1734, NCI-H1755, NCI-H1792, NCI-H1838, NCI-H1869, NCI-H1876, NCI-H1882, NCI-H1915, NCI-H196, NCI-H1975, NCI-H2029, NCI-H2030, NCI-H2066, NCI-H2073, NCI-H2081, NCI-H2085, NCI-H211, NCI-H2110, NCI-H2122, NCI-H2126, NCI-H2141, NCI-H2170, NCI-H2172, NCI-H2196, NCI-H226, NCI-H2286, NCI-H2291, NCI-H23, NCI-H2342, NCI-H2347, NCI-H2405, NCI-H2444, NCIH292, NCIH358M, NCI-H446, NCIH460, NCI-H508, NCI-H520, NCI-H522, NCI-H524, NCI-H596, NCI-H647, NCI-H661, NCI-H69, NCI-H774, NCIH82, NCI-H841, NGP, PC-9, RKO, SCLC-21 h, SHP-77, SK-CO-1, SK-MES-1, SNU-C1, SW1116, SW1417, SW1463, SW48, SW620, SW837, SW 900, SW948, T3M-11, T3M-12, T84, A110L, A-427, A529L, A549, BEN, CACO2, CALU-1, Calu-3, CALU6, COL0205, COLO-677, COL0678, COLO-699, COR-L311, COR-L88, DLD1, DMS 114, DMS 153, DMS 454, DMS 53, DV-90, EBC-1, EPLC-272H, H-2171, H69V, HCC-15, HCC2935, HCC-366, HCC-44, HCC-827, HCT116, HCT15, HLC-1, HLF-a, H-MESO-1, HT29, IA-LM, IMR90, JU77, LC-2/ad, LK-2, L068, LOVO, LS123, LS411N, LU65, Lu99B, LUDLU-1, LXF-289, MIAPACA2, MS-1, MSTO-211H, NCI-H1048, NCI-H1105, NCI-H1299, NCI-H146, NCI-H1563, NCI-H1568, NCI-H1573, NCI-H1581, NCI-H1651, NCI-H1694, NCI-H1734, NCI-H1755, NCI-H1792, NCI-H1838, NCI-H1869, NCI-H1876, NCI-H1882, NCI-H1915, NCI-H196, NCI-H1975, NCI-H2029, NCI-H2030, NCI-H2066, NCI-H2073, NCI-H2081, NCI-H2085, NCI-H211, NCI-H2110, NCI-H2122, NCI-H2126, NCI-H2141, NCI-H2170, NCI-H2172, NCI-H2196, NCI-H226, NCI-H2286, NCI-H2291, NCI-H23, NCI-H2342, NCI-H2347, NCI-H2405, NCI-H2444, NCIH292, NCIH358M, NCI-H446, NCIH460, NCI-H508, NCI-H520, NCI-H522, NCI-H524, NCI-H596, NCI-H647, NCI-H661, NCI-H69, NCI-H774, NCIH82, NCI-H841, NGP, PC-9, RKO, SCLC-21 h, SHP-77, SK-CO-1, SK-MES-1, SNU-C1, SW1116, SW1417, SW1463, SW48, SW620, SW837, SW 900, SW948, T3M-11, T3M-12, and T84.

Combination and monotherapy treatment effects were compared for the two major tissues of origins, colon and lung, but for some aspects also data of the four pleura derived cell lines are considered.

Over all the combination of etoposide with Compound 1 demonstrated an increase in growth inhibition for the cell lines analyzed. The combination effects are synergistic for most cell lines in the combination with Compound 1.

Details of the assay protocol are set forth below.

128 cell lines were screened with variable doses of etoposide (2.44E-09M, 9.77E-09M, 3.91E-08M, 1.56E-07M, 6.25E-07M, 2.50E-06M, 1.00E-05M) and fixed doses of Compound 1 (0.3 µM). Single agent as well as combination treatment growth inhibition effects were measured by ONCOLEAD.

Growth inhibition data relative to an untreated control were received as individual measures and have been modeled as a 4-parametric dose-response curve using the DRC package in R (1). The inhibitor concentrations at 50% growth-inhibition (GI50) were obtained using the crossing point of the dose-response curve with the 50% growth inhibition level.

Relative area above the dose-response curve (relAOC or AOC) were obtained as the area above the dose-response curve in the dose range between 1E-3M and 1E-10M.

Combination effects of etoposide with Compound 1 were calculated under the assumption of independent modes of action of the combination partners. Synergy of the treatment effect was assessed using the BLISS independence model (2) as the average excess over the linear combination of the monotherapy treatments effects at the different data points measured. The synergy scores were provided by ONCOLEAD.

Treatment effects are summarized as area above the dose-response curve (AOC) or as the concentration needed to reach 50% growth inhibition relative to control cells (GI50). AOC values were obtained for 122 cell lines of the three major tissues of origin, colon, lung and pleura. The sensitivity against the combination treatment is higher in nearly all (120/122) cases which is indicated by longer red bars in the AOC ratio plot in FIG. 15 (Antitumor Effect of Compound 1 in Combination with etoposide in the Lung and Colon Cancer Cell Line Panels in vitro). FIG. 16 depicts Antitumor Effect of Compound 1 in Combination with etoposide in the Lung and Colon Cancer Cell Line Panels in vitro.

Median etoposide concentration needed to reach GI50 is shifted in lung cancer cell lines from: 0.32 µM for monotherapy to 0.04 µM in combination with Compound 1.

Median etoposide concentration needed to reach GI50 is shifted in colon cancer cell lines from 0.7 µM for monotherapy to 0.12 µM in combination with Compound 1.

Median etoposide concentration needed to reach GI50 is shifted in mesothelioma cell lines from 1 µM for monotherapy to 0.11 µM in combination with Compound 1.

The GI50 shift for the four major lung tumor subtypes small cell carcinoma, adenocarcinoma, squamous cell carcinoma, and large cell carcinoma in the combination of etoposide with Compound 1, both the squamous as well as the large cell carcinomas are equally sensitized to the combination treatment. The combination in those two indications result in 12.8-fold lower concentration of etoposide needed to reach at G150 when administered in combination with Compound 1.

Synergy scores were provided by ONCOLEAD as mean excess over the linear combination of the monotherapy effects over the individual measurements.

Figure 15:
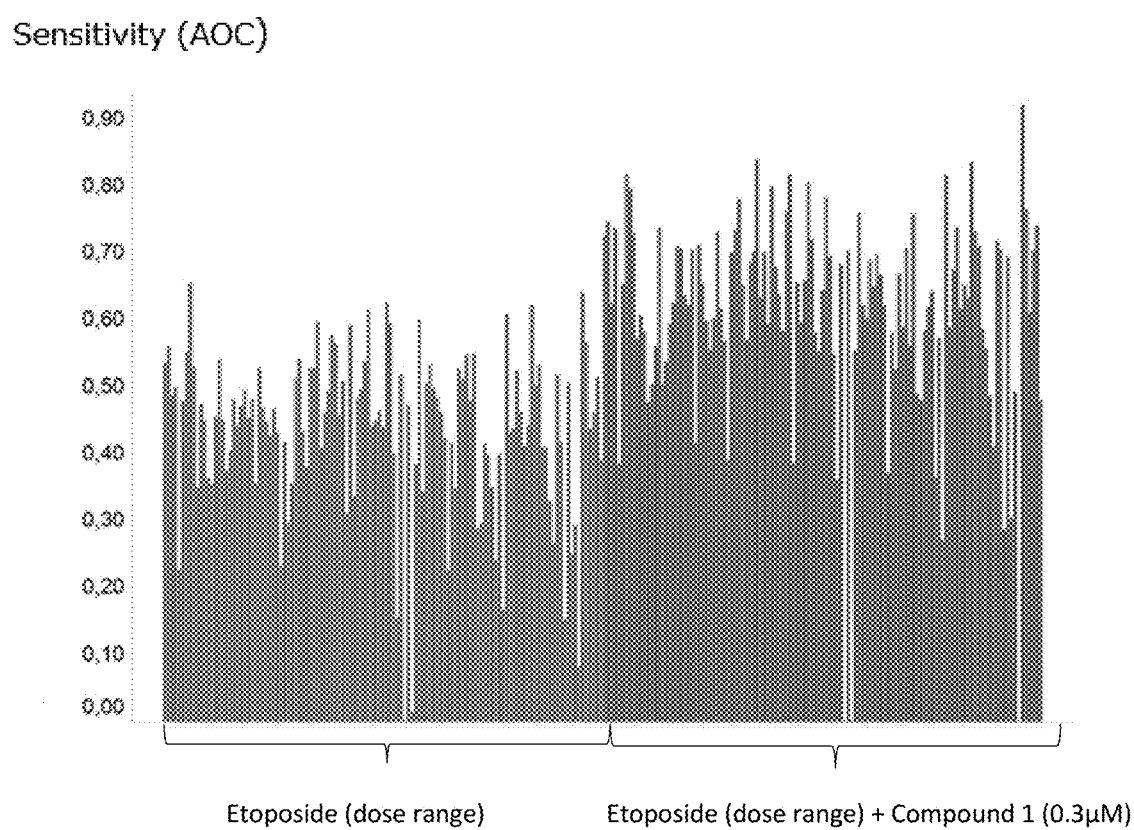
FIG. 15 shows the results of the combination of Compound 1 with Etoposide in the cancer cell line panels in vitro.
Figure 16:
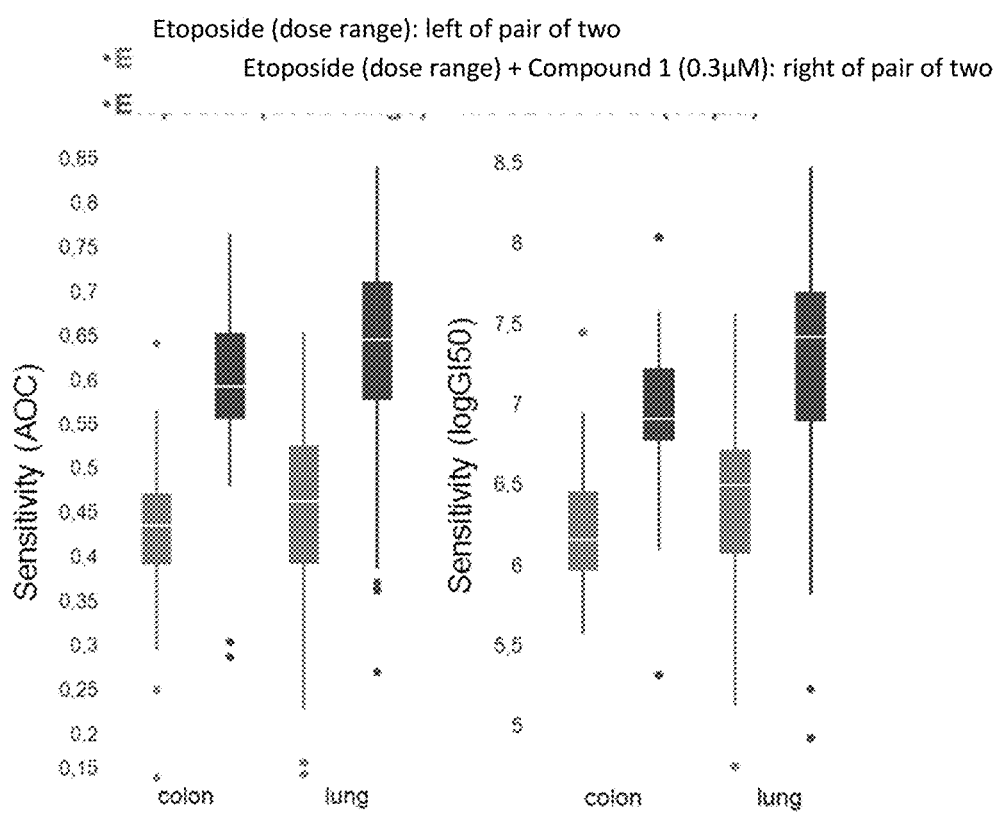
FIG. 16 shows the results of the combination of Compound 1 with Etoposide in cancer cell line panels in vitro.

Synergy score distributions for the Compound 1 combination treatments are shown in FIG. 15 as scatter plots of individual cell line data points. Synergy levels within 10% above or below the linear combination effects could be seen as 'close to linear' effect.

Figure 17:
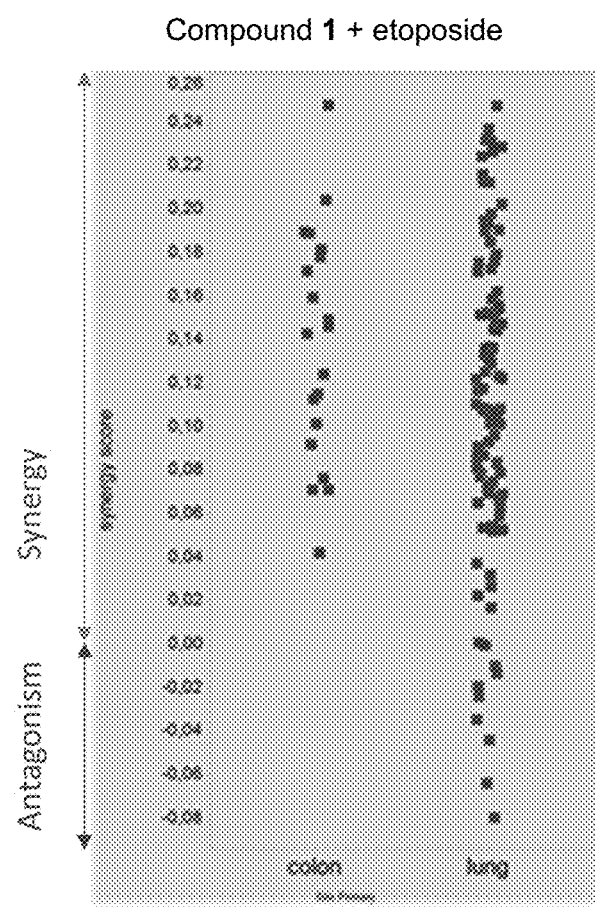
FIG. 17 shows the synergistic results of the combination of Compound 1 with Etoposide.

As shown in FIG. 17, 15 of 20 colon, 2 of 4 pleura (not shown), and 58 of 97 lung cell lines show a synergistic effect between etoposide and Compound 1. The other cell lines shows a linear or close to linear combination effect of those two compounds.

Example 7

Compound 1 was evaluated to determine the shift in activity of etoposide in multiple cancer cell lines. Compound 1 was used in DMSO solution in the following concentrations: 150 nM, 300 nM, and 1 µM. Etoposide was used in DMSO solution in the following concentrations: 10 µM, 2.5 µM, 630 nM, 156 nM, 39 nM, 9.8 nM, and 2.4 nM.

Cell lines were purchased directly from the ATCC, NCI, CLS and DSMZ cell line collections. A master bank and working aliquots were prepared. Cells used for the study in vitro potentiation study using a 200+ cell line panel had undergone less than 20 passages. To ensure the absence of potential contamination or wrong assignment, all cell lines were tested by STR analysis. Absence of mycoplasma and SMRV contamination was confirmed for all cell lines used in the studies.

The cell lines were grown in the media recommended by the suppliers in the presence of 100 U/ml penicillin G and 100 µg/ml streptomycin supplemented with 10% FCS. RPMI 1640, and DMEM were supplemented with 2 mM L-glutamine and 1 mM Na-pyruvate.

MEM Earle's medium had additionally 1% NEAA. Some cell lines required additional supplements such as 2.5% horse serum, hydrocortisone, transferrin, beta-estradiol, selenite and 1 unit/ml insulin.

RPMI medium was used for culturing the following cell lines: 5637, 22RV1, 7860, A2780, A431, A549, ACHN, ASPC1, BT20, BXPC3, CAKI1, CLS439, COLO205, COLO678, DLD1, DU145, EF021, EJ28, HCT15, HS578T, IGROV1, JAR, LOVO, MCF7, MDAMB231, MDAMB435, MDAMB436, MDAMB468, MHHES1, MT3, NCIH292, NCIH358M, NCIH460, NCIH82, OVCAR3, OVCAR4, PANC1005 (addition of insulin), PBMC, PC3, RDES, SF268, SF295, SKBR3, SKMEL28, SKMEL5, SKOV3, SW620, U20S, UMUC3, U031, GRANTA-519, SU-DHL-6, SU-DHL-10, RAMOS, MINO, HL-60, K-562, THP-1, L-363, WSU-NHL, and MV4-11. The following lung and colorectal cancer cell lines were cultured RPMI:

NCI-H23 NCI-H1838 NCI-H2347 LS411N H-2171 NCI-H2122 NCI-H1915 NCI-H1299 COR-L88 COLO-677 DV-90 NCI-H69 MS-1 NCI-H211 NCI-H524 SCLC-21 h COR-L311 T3M-12 NCI-H146 NCI-H2030 NCI-H1792 HCC-44 H69V NCIH292 COL0678 NCI-H508 SNU-C1

DMEM medium was used to culture A204, A375, A673, C33A, CASKI, HCT116, HEPG2, HS729, HT29, J82, MG63, MIAPACA2 (addition of horse serum), PANC1, PLCPRF5, RD, SAOS2, SKLMS1, SKNAS, SNB75, T24, and TE671.

MEM Earle's medium was used for CACO2, CALU6, HEK293, HELA, HT1080, IMR90, JEG3, JIMT1, SKHEP1, SKNSH, and U87MG.

DMEM/F12 medium was used for NCI-H2066, NCI-H2029, NCI-H2444, H-MESO-1, NCI-H2085, LC-2/ad, DMS114, NCI-H2126, SW948, T84, NCI-H2405, SW1463, SW1116, A110L, T3M-11, JU77, NCI-H596, NCI-H1048, NCI-H226, NCI-H2073, HLF-a, NCI-H2342, NCI-H1734, NCI-H2196, DMS454, NCI-H1882, NCI-H1876, HCC2935, NCI-H2286, NCI-H2110, NCI-H2291, IA-LM, NCI-H1755, NCI-H522, SW1417, SW837, SW48, NCI-H520, COLO-699, BEN, NCI-H1573, NCI-H1975, NCI-H2170, HCC-827, L068, NCI-H841, SHP-77, SW900, LXF-289, NCI-H661, NCI-H1581, HCC-15, SK-MES-1, NCI-H647, LUDLU-1, HLC-1, EBC-1, LU65, CALU-1, PC-9, A-427, LK-2, MSTO-211H, Lu99B, NCI-H2141, NCI-H1105, NCI-H774, NCI-H1694, NCI-H2081, NCI-H1869, Calu-3, EPLC-272H, HCC-366, DMS 53, NCI-H1651, NCI-H2172, NCI-H1563, NCI-H1568, NCI-H446, A529L, NCI-H196, DMS 153, and NGP.

Cells were grown in 5% CO2 atmosphere in a NB-203-XXL incubator (N-Biotec, South Korea).

Cell growth and treatment were performed in 96-well microtitre plates CELLSTAR® (Greiner Bio-One, Germany). Cells harvested from exponential phase cultures by trypsinization or by splitting (in the case of cells growing in suspension) were plated in 90 µl of media at optimal seeding densities. The optimal seeding density for each cell line was determined to ensure exponential growth for the duration of the experiment. All cells growing without anticancer agents were sub-confluent by the end of the treatment, as determined by visual inspection.

Compound dilutions in DMSO were performed in 96-well 0.5 ml MTP plates (Greiner Bio-One, Germany). Compounds were then diluted 1:100 in RPMI medium.

90 µl of cells, after a 48-hour pre-growth period, were treated by mixing with 10 µl of the compound-containing media (resulting in a final DMSO concentration of 0.1%). The cells were allowed to grow at 37° C. for 72 (or 120) hours.

In addition, all experiments contained a few plates with cells that were analyzed immediately after the 48 hours recovery period. These plates contained information about the cell number, Tz, at time zero (see 3.5.1) i.e. before treatment, and served to calculate the cytotoxicity.

In the case of combination both agents were mixed together in DMSO at equal volumes so that final concentration of DMSO was 0.2%.

Measurements were performed using a total protein staining protocol [Vichai and Kirtikara, 2006]. Cells were fixed to the surface by addition of 10% TCA (for adherent growing cells) or 50% TCA (for semi-adherent growing cell or cells growing in suspension). After an hour of incubation at 4° C. plates were washed twice with 200 µl of deionized water and dried. Cells were then stained with 100 µl of 0.04% w/v SRB. The plates were incubated at room temperature for at least 30 min and washed six times with 1% acetic acid to remove unbound stain. The plates were left to dry at room temperature and bound SRB was solubilized with 100 µl of 10 mM Tris base. Optical density was measured at 492, 520, and 560 nm using a Deelux-LED96 plate reader (Deelux Labortechnik GmbH, Germany).

The non-linear curve fitting calculations were performed using algorithms and visualization tools developed in-house. The algorithms are similar to those previously described [DeLean et al., 1978] and were complemented with the mean square error or MSE model.

This can be compared to commercial applications, e.g. XLfit (ID Business Solutions Ltd., Guildford, UK) algorithm "205". The calculations included the dose response curves with the best approximation line, a 95% confidence interval for the 50% effect (see below).

One common way to express the effect of an anticancer agent is to measure cell viability and survival in the presence of the test agent as % T/C×100. The relationship between viability and dose is called a dose response curve. Two major values are used to describe this relationship without needing to show the curve: the concentration of test agents giving a % T/C value of 50%, or 50% growth inhibition (IC50), and a % T/C value of 10%, or 90% growth inhibition (IC90).

Using these measurements, cellular responses can be calculated for incomplete inhibition of cell growth (GI), complete inhibition of cell growth (TGI) and net loss of cells (LC) due to compound activity. Growth inhibition of 50% (GI50) is calculated as $100 \times [(Ti-Tz)/(C-Tz)]=50$. This is the drug concentration causing a 50% reduction compared to the net protein increase in control cells during the drug incubation period. In other words, GI50 is IC50 corrected for time zero. Similar to IC90, calculated GI90 values are also reported for all compounds tested. TGI was calculated from Ti=Tz. LC50, is the concentration of drug causing a 50% reduction in the measured protein at the end of the drug incubation period compared to that at the beginning. It was calculated as $100 \times [(Ti-Tz)/Tz]=-50$.

The activity of Etoposide and Compound 1 was investigated previously in a panel of 81 cancer cell lines representing 17 tumor tissue types, plus resting, non-proliferating PBMC (total 82 cell lines), which were used to detect activity beyond affecting cell proliferation.

Etoposide showed broad, more than 1000-fold, activity ranging from 30 nM in JEG3 cell lines to above 10 µM, e.g. JIMT1 and COLO678. For 3 cell lines GI50 values could only be estimated above 10 µM, and for 14 cell lines no activity above 10 µM could be recorded (including resting PBMC).

Compound 1 showed a narrow but more than 20-fold activity range, from 500 nM in a set of cell lines to above 10 µM. For some cell lines, GI50 values could only be estimated above 10 µM. No activity in resting PBMC could be detected.

The overall effect of the combination of Compound 1 and etoposide was evaluated by comparing GI50 values alone and in combination. Addition of Compound 1 significantly increased both the activity range and potency of Etoposide in combination. Table 3 summarizes etoposide activity alone and in combination with Compound 1. The * or ** mark the lowest or highest tested concentrations. Etoposide-Compound 1-150 nM and Etoposide-Compound 1-1 uM were tested in a panel of 93 cell lines. Etoposide-Compound 1-300 nM was tested in a panel of 127 cell lines enriched for lung and colorectal cancer cell lines and with 120 hours of treatment. In the [ ] brackets 120 hour-treatment results are shown. Both uM and µM stand for micromolar.

TABLE 3

| Agent | Average GI50 in µM | Median GI50 in µM | Most sensitive cell line(GI50) | Most resistant cell line(GI50) |
|---|---|---|---|---|
| Etoposide | 1.7 [0.7] | 0.9 [0.4] | MV4-11 (38 nM) [COLO-677 15 nM] | 6 [5] cell lines >10 µM** |
| Etoposide-Compound 1-150 nM | 0.8 | 0.3 | MV4-11 (5 nM) | 1 cell line >10 µM** |
| Etoposide-Compound 1-300 nM | 0.17 | 0.04 | [5 cell lines <2 nM*] | SNU-C1, 4.5 µM |
| Etoposide-Compound 1-1 uM | 0.16 | 0.03 | 25 cell lines (<2 nM*) | 1 cell line >10 µM** |

TABLE 4 provides the potentiation of etoposide and Compound 1 calculated as GI50 (93 cell lines panel).

| | | µM (±Compound 1) | | | Combination | Effect | |
|---|---|---|---|---|---|---|---|
| Origin | Cell line | Etoposide | +150 nM | +1 µM | Average | +150 nM | +1 µM |
| breast | MCF7 | 1.287 | 0.209 | <0.002 | −0.18 | 0.20 | 0.74 |
| breast | MDAMB468 | 1.169 | 0.467 | 0.027 | −0.38 | 0.09 | 0.35 |
| prostate | 22RV1 | 0.234 | 0.063 | 0.002 | −0.23 | 0.12 | 0.39 |
| bladder | 5637 | 0.685 | 0.183 | 0.019 | −0.83 | 0.06 | 0.21 |
| kidney | 786O | 0.928 | 0.295 | 0.044 | −0.38 | 0.05 | 0.27 |
| muscle | A204 | 0.286 | 0.019 | <0.002 | −0.11 | 0.28 | 0.63 |
| ovary | A2780 | 0.062 | 0.023 | 0.001 | −0.33 | 0.09 | 0.45 |
| skin | A375 | 0.378 | 0.083 | 0.012 | −0.24 | 0.23 | 0.28 |
| breast | MCF7 | 1.287 | 0.209 | <0.002 | −0.18 | 0.20 | 0.74 |
| breast | MDAMB468 | 1.169 | 0.467 | 0.027 | −0.38 | 0.09 | 0.35 |

TABLE 4-continued provides the potentiation of etoposide and Compound 1 calculated as GI50 (93 cell lines panel).

| | | μM (±Compound 1) | | | Combination Effect | | |
|---|---|---|---|---|---|---|---|
| Origin | Cell line | Etoposide | +150 nM | +1 μM | Average | +150 nM | +1 μM |
| skin | A431 | 1.522 | 0.355 | 0.011 | −0.36 | 0.11 | 0.40 |
| lung | A549 | 0.390 | 0.067 | 0.003 | −0.49 | 0.11 | 0.42 |
| muscle | A673 | 1.075 | 0.308 | 0.039 | −0.75 | −0.01 | 0.15 |
| kidney | ACHN | 0.714 | 0.202 | <0.002 | −0.25 | 0.20 | 0.50 |
| pancreas | ASPC1 | >10 | 8.757 | 0.797 | −0.09 | 0.10 | 0.33 |
| breast | BT20 | 0.073 | 0.052 | 0.017 | −0.09 | 0.11 | 0.27 |
| pancreas | BXPC3 | 7.144 | 3.797 | 0.363 | −0.09 | 0.11 | 0.33 |
| cervix | C33A | 0.393 | 0.126 | 0.022 | −0.44 | 0.05 | 0.25 |
| colon | CACO2 | 3.648 | 2.550 | 0.733 | −0.12 | 0.04 | 0.22 |
| kidney | CAKI1 | 0.520 | 0.046 | 0.001 | −0.29 | 0.27 | 0.54 |
| lung | CALU6 | 3.651 | 1.782 | 0.815 | −0.38 | 0.00 | 0.12 |
| cervix | CASKI | 1.454 | 0.571 | 0.016 | −0.22 | 0.11 | 0.50 |
| bladder | CLS439 | 0.965 | 0.403 | 0.007 | −0.09 | 0.15 | 0.36 |
| colon | COLO205 | 1.046 | 0.406 | 0.077 | −0.74 | −0.04 | 0.13 |
| colon | COLO678 | 10.815 | 6.035 | 1.387 | −0.14 | 0.06 | 0.17 |
| colon | DLD1 | 1.350 | 0.595 | 0.061 | −0.36 | 0.04 | 0.23 |
| breast | MCF7 | 1.287 | 0.209 | <0.002 | −0.18 | 0.20 | 0.74 |
| breast | MDAMB468 | 1.169 | 0.467 | 0.027 | −0.38 | 0.09 | 0.35 |
| prostate | DU145 | 0.701 | 0.235 | 0.022 | −0.33 | 0.07 | 0.31 |
| ovary | EFO21 | 8.221 | 4.468 | <0.002 | 0.01 | 0.25 | 0.58 |
| bladder | EJ28 | 0.440 | 0.061 | 0.011 | −1.21 | 0.02 | 0.14 |
| hematological | GRANTA-519 | 0.247 | 0.098 | 0.008 | −0.29 | 0.05 | 0.41 |
| colon | HCT116 | 0.770 | 0.328 | 0.048 | −0.44 | 0.00 | 0.27 |
| colon | HCT15 | 1.466 | 0.703 | 0.066 | −0.37 | 0.04 | 0.22 |
| kidney | HEK293 | 0.190 | 0.073 | 0.006 | −0.36 | 0.03 | 0.41 |
| cervix | HELA | 2.363 | 0.875 | 0.251 | −0.35 | 0.04 | 0.19 |
| liver | HEPG2 | 0.806 | 0.202 | 0.016 | −0.58 | −0.02 | 0.23 |
| hematological | HL-60 | 0.120 | 0.056 | 0.005 | −0.29 | 0.07 | 0.35 |
| breast | HS578T | 0.874 | 0.106 | 0.001 | −0.37 | 0.10 | 0.42 |
| muscle | HS729 | 0.730 | 0.521 | 0.095 | −0.26 | 0.07 | 0.21 |
| connective tissue | HT1080 | 0.096 | 0.019 | 0.004 | −1.12 | −0.03 | 0.10 |
| colon | HT29 | 2.223 | 1.698 | 0.315 | −0.18 | 0.02 | 0.30 |
| ovary | IGROV1 | 1.056 | 0.322 | <0.002 | −0.11 | 0.11 | 0.73 |
| lung | IMR90 | 0.704 | 0.032 | <0.002 | −0.02 | 0.36 | 0.66 |
| breast | MCF7 | 1.287 | 0.209 | <0.002 | −0.18 | 0.20 | 0.74 |
| breast | MDAMB468 | 1.169 | 0.467 | 0.027 | −0.38 | 0.09 | 0.35 |
| bladder | J82 | 7.930 | 3.541 | 1.322 | −0.34 | −0.01 | 0.19 |
| placenta | JAR | 0.116 | 0.017 | 0.001 | −0.83 | 0.09 | 0.28 |
| placenta | JEG3 | 0.041 | 0.014 | 0.003 | −0.61 | 0.08 | 0.20 |
| breast | JIMT1 | 17.654 | 1.380 | 0.047 | −0.23 | 0.10 | 0.33 |
| hematological | K-562 | 0.277 | 0.067 | 0.008 | −0.75 | 0.05 | 0.20 |
| hematological | KASUMI-1 | 0.494 | 0.170 | <0.002 | −0.16 | 0.12 | 0.64 |
| hematological | L-363 | 0.327 | 0.121 | 0.004 | −0.26 | 0.02 | 0.52 |
| colon | LOVO | 0.606 | 0.105 | 0.001 | −0.16 | 0.25 | 0.53 |
| breast | MDAMB231 | 1.941 | 0.480 | 0.135 | −0.66 | 0.05 | 0.13 |
| skin | MDAMB435 | 1.143 | 0.529 | 0.070 | −0.35 | 0.05 | 0.28 |
| breast | MDAMB436 | 0.378 | 0.101 | 0.007 | −0.16 | 0.12 | 0.38 |
| bone | MG63 | 1.020 | 0.944 | 0.199 | −0.29 | −0.02 | 0.11 |
| bone | MHHES1 | 0.227 | 0.053 | 0.006 | −0.77 | 0.05 | 0.24 |
| pancreas | MIAPACA2 | 0.689 | 0.178 | 0.045 | −0.92 | 0.03 | 0.16 |
| hematological | MINO | 0.236 | 0.081 | <0.002 | −0.30 | 0.06 | 0.49 |
| breast | MT3 | 0.609 | 0.179 | 0.009 | −0.41 | 0.00 | 0.36 |
| breast | MCF7 | 1.287 | 0.209 | <0.002 | −0.18 | 0.20 | 0.74 |
| breast | MDAMB468 | 1.169 | 0.467 | 0.027 | −0.38 | 0.09 | 0.35 |
| hematological | MV4-11 | 0.038 | 0.005 | <0.002 | −0.15 | 0.30 | 0.67 |
| lung | NCIH292 | 1.650 | 0.131 | <0.002 | −0.28 | 0.15 | 0.70 |
| lung | NCIH358M | 3.331 | 1.168 | 0.001 | −0.15 | 0.13 | 0.39 |
| lung | NCIH460 | 0.167 | 0.059 | 0.004 | −0.47 | 0.05 | 0.37 |
| lung | NCIH82 | 1.150 | 0.503 | 0.075 | −0.32 | 0.06 | 0.29 |
| ovary | OVCAR3 | 2.542 | 0.620 | <0.002 | −0.12 | 0.17 | 0.55 |
| ovary | OVCAR4 | >10 | >10 | >10 | −0.08 | 0.13 | 0.26 |
| pancreas | PANC1 | 1.925 | 0.533 | 0.065 | −0.23 | 0.12 | 0.15 |
| pancreas | PANC1005 | 2.733 | 0.998 | 0.123 | −0.22 | 0.08 | 0.24 |
| hematological | PBMC | >10 | >10 | >10 | −0.35 | 0.01 | 0.07 |
| prostate | PC3 | 5.235 | 2.163 | <0.002 | −0.04 | 0.21 | 0.53 |
| liver | PLCPRF5 | 6.252 | 3.184 | 1.884 | −0.22 | 0.01 | 0.16 |
| hematological | RAMOS | 0.204 | 0.031 | <0.002 | −0.24 | 0.20 | 0.63 |
| muscle | RD | >10 | 4.262 | 0.932 | −0.29 | 0.01 | 0.15 |
| bone | RDES | 0.412 | 0.152 | 0.012 | −0.52 | 0.06 | 0.34 |
| bone | SAOS2 | 1.456 | 0.789 | 0.004 | −0.21 | 0.09 | 0.48 |
| breast | MCF7 | 1.287 | 0.209 | <0.002 | −0.18 | 0.20 | 0.74 |
| breast | MDAMB468 | 1.169 | 0.467 | 0.027 | −0.38 | 0.09 | 0.35 |
| brain | SF268 | 1.967 | 1.044 | 0.189 | −0.46 | 0.05 | 0.17 |
| brain | SF295 | 1.161 | 0.341 | 0.038 | −0.57 | 0.11 | 0.22 |

TABLE 4-continued provides the potentiation of etoposide and Compound 1 calculated as GI50 (93 cell lines panel).

| | | μM (±Compound 1) | | | Combination | Effect | |
|---|---|---|---|---|---|---|---|
| Origin | Cell line | Etoposide | +150 nM | +1 μM | Average | +150 nM | +1 μM |
| breast | SKBR3 | 0.432 | 0.224 | 0.055 | −0.22 | 0.08 | 0.33 |
| liver | SKHEP1 | 0.083 | 0.021 | 0.005 | −0.61 | 0.08 | 0.07 |
| uterus | SKLMS1 | 1.636 | 0.598 | <0.002 | −0.23 | 0.05 | 0.29 |
| skin | SKMEL28 | 1.887 | 0.828 | 0.120 | −0.19 | 0.15 | 0.30 |
| skin | SKMEL5 | 0.558 | 0.123 | 0.009 | −0.85 | 0.03 | 0.25 |
| brain | SKNAS | 2.146 | 0.914 | 0.193 | −0.49 | 0.06 | 0.11 |
| brain | SKNSH | 0.265 | 0.099 | <0.002 | −0.38 | 0.13 | 0.53 |
| ovary | SKOV3 | 2.986 | 1.800 | 0.286 | −0.06 | 0.11 | 0.40 |
| brain | SNB75 | 3.794 | 2.103 | 0.012 | −0.27 | 0.08 | 0.45 |
| hematological | SU-DHL-6 | 0.665 | 0.089 | <0.002 | −0.03 | 0.36 | 0.94 |
| colon | SW620 | 0.302 | 0.097 | 0.018 | −0.60 | 0.03 | 0.17 |
| bladder | T24 | 2.527 | 1.780 | 0.630 | −0.31 | 0.04 | 0.04 |
| muscle | TE671 | 1.146 | 0.373 | 0.038 | −0.32 | 0.08 | 0.23 |
| hematological | THP-1 | 0.110 | 0.035 | <0.002 | −0.10 | 0.16 | 0.49 |
| breast | MCF7 | 1.287 | 0.209 | <0.002 | −0.18 | 0.20 | 0.74 |
| breast | MDAMB468 | 1.169 | 0.467 | 0.027 | −0.38 | 0.09 | 0.35 |
| bone | 152OS | 1.078 | 0.314 | 0.038 | −0.34 | 0.05 | 0.21 |
| brain | 1587MG | 2.400 | 0.469 | 0.007 | −0.12 | 0.15 | 0.43 |
| bladder | 15M15C3 | 0.604 | 0.153 | 0.038 | −0.66 | 0.06 | 0.18 |
| kidney | 15O31 | 7.911 | 1.174 | 0.050 | −0.29 | 0.17 | 0.42 |
| hematological | WS15-NHL | 0.149 | 0.036 | <0.002 | −0.11 | 0.28 | 0.93 |

TABLE 5

Potentiation of Etoposide and Compound 1 calculated as GI50 (127 cell lines panel)

| | | μM (±Compound 1) | | Combination | Effect |
|---|---|---|---|---|---|
| Origin | Cell line | Etoposide | +300 nM | Average | +300 nM |
| lung | L15DL15-1 | 1.09 | 0.08 | −0.56 | 0.19 |
| lung | MS-1 | 0.25 | 0.06 | −0.20 | 0.08 |
| lung | A-427 | 0.10 | 0.01 | −0.47 | 0.29 |
| lung | A110L | 0.17 | 0.01 | −0.99 | 0.12 |
| lung | LUDLU-1 | 1.09 | 0.08 | −0.56 | 0.19 |
| lung | MS-1 | 0.25 | 0.06 | −0.20 | 0.08 |
| lung | A529L | 0.47 | 0.09 | −0.25 | 0.06 |
| lung | A549 | 0.17 | 0.01 | −0.47 | 0.30 |
| lung | BEN | 1.39 | 0.24 | −0.11 | 0.23 |
| colon | CACO2 | 0.87 | 0.13 | −0.23 | 0.09 |
| lung | CALU-1 | 0.29 | 1.08 | −0.31 | −0.12 |
| lung | CALU6 | 0.25 | 0.03 | −0.86 | 0.08 |
| lung | COLO-677 | 0.02 | 0.00 | −0.52 | 0.13 |
| lung | COLO-699 | 1.14 | 0.15 | −0.13 | 0.28 |
| colon | COLO205 | 0.35 | 0.05 | −0.64 | 0.04 |
| colon | COLO678 | 0.62 | 0.08 | −0.16 | 0.14 |
| lung | COR-L311 | 0.31 | 0.06 | −0.30 | 0.10 |
| lung | COR-L88 | 1.03 | 0.37 | −0.22 | 0.03 |
| lung | Calu-3 | 0.03 | 0.00 | −0.60 | 0.06 |
| colon | DLD1 | 0.45 | 0.09 | −0.34 | 0.09 |
| lung | DMS 114 | 0.32 | 0.04 | −0.39 | 0.13 |
| lung | DMS 153 | 0.17 | 0.09 | −0.11 | 0.01 |
| lung | LUDLU-1 | 1.09 | 0.08 | −0.56 | 0.19 |
| lung | MS-1 | 0.25 | 0.06 | −0.20 | 0.08 |
| lung | DMS 454 | 2.46 | 0.49 | −0.17 | 0.15 |
| lung | DMS 53 | 0.71 | 0.02 | −0.13 | 0.34 |
| lung | DV-90 | 0.22 | 0.03 | −0.30 | 0.14 |
| lung | EBC-1 | 1.17 | 0.10 | −0.47 | 0.19 |
| lung | EPLC-272H | 0.26 | 0.01 | −0.44 | 0.27 |
| lung | H-2171 | 0.29 | 0.05 | −0.25 | 0.11 |
| lung | H-MESO-1 | 0.73 | 0.05 | −0.40 | 0.19 |
| lung | H69V | 0.68 | 0.08 | −0.58 | 0.09 |
| lung | HCC-15 | 0.21 | 0.01 | −0.49 | 0.21 |
| lung | HCC-366 | 3.02 | 1.02 | −0.09 | 0.12 |
| lung | HCC-44 | 0.28 | 0.03 | −0.35 | 0.18 |
| lung | HCC-827 | 0.32 | 0.03 | −0.35 | 0.17 |
| lung | HCC2935 | 1.60 | 0.33 | −0.07 | 0.19 |
| colon | HCT116 | 0.75 | 0.16 | −0.43 | 0.04 |
| colon | HCT15 | 0.57 | 0.10 | −0.41 | 0.08 |
| lung | HLC-1 | 0.85 | 0.02 | −0.13 | 0.43 |
| lung | LUDLU-1 | 1.09 | 0.08 | −0.56 | 0.19 |
| lung | MS-1 | 0.25 | 0.06 | −0.20 | 0.08 |
| lung | HLF-a | >10 | 1.28 | 0.02 | 0.45 |
| colon | HT29 | 1.08 | 0.13 | −0.70 | 0.09 |
| lung | IA-LM | 0.93 | 0.01 | 0.11 | 0.44 |
| lung | IMR90 | 0.40 | 0.00 | −0.05 | 0.53 |
| lung | JU77 | 2.39 | 0.23 | −0.07 | 0.28 |
| lung | LC-2/ad | 0.23 | 0.01 | −0.33 | 0.27 |
| lung | LK-2 | 0.22 | 0.02 | −0.61 | 0.25 |
| lung | LO68 | 1.09 | 0.11 | −0.12 | 0.24 |
| colon | LOVO | 0.36 | 0.04 | −0.09 | 0.33 |
| colon | LS123 | 0.76 | 0.06 | −0.14 | 0.22 |
| colon | LS411N | 0.23 | 0.03 | −0.62 | 0.09 |
| lung | LU65 | 0.22 | 0.01 | −0.94 | 0.06 |
| lung | LXF-289 | 0.61 | 0.03 | −1.07 | 0.15 |
| lung | Lu99B | 0.13 | 0.01 | −0.71 | 0.23 |
| pancreas | MIAPACA2 | 0.31 | 0.04 | −0.75 | 0.11 |
| lung | MSTO-211H | 0.09 | 0.01 | −0.36 | 0.30 |
| lung | LUDLU-1 | 1.09 | 0.08 | −0.56 | 0.19 |
| lung | MS-1 | 0.25 | 0.06 | −0.20 | 0.08 |
| lung | NCI-H1048 | 0.09 | 0.00 | −0.07 | 0.49 |
| lung | NCI-H1105 | 0.19 | 0.07 | −0.09 | 0.10 |
| lung | NCI-H1299 | 0.57 | 0.04 | −0.97 | 0.10 |
| lung | NCI-H146 | 0.08 | 0.02 | −0.21 | 0.01 |
| lung | NCI-H1563 | 4.46 | 0.00 | −0.06 | 0.56 |
| lung | NCI-H1568 | 0.08 | 0.00 | −0.31 | 0.35 |
| lung | NCI-H1573 | 1.13 | 0.47 | 0.07 | 0.16 |
| lung | NCI-H1581 | 0.25 | 0.01 | −0.31 | 0.28 |
| lung | NCI-H1651 | 0.14 | 0.03 | −0.04 | 0.23 |
| lung | NCI-H1694 | 0.21 | 0.04 | −0.42 | 0.04 |
| lung | NCI-H1734 | 0.04 | 0.00 | −0.29 | 0.35 |
| lung | NCI-H1755 | 0.98 | 0.05 | −0.17 | 0.38 |
| lung | NCI-H1792 | 0.88 | 0.16 | −0.54 | 0.06 |
| lung | NCI-H1838 | 0.19 | 0.04 | 0.03 | 0.29 |
| lung | NCI-H1869 | 0.49 | 0.01 | −0.16 | 0.28 |
| lung | NCI-H1876 | 0.03 | 0.00 | −0.05 | 0.35 |
| lung | LUDLU-1 | 1.09 | 0.08 | −0.56 | 0.19 |
| lung | MS-1 | 0.25 | 0.06 | −0.20 | 0.08 |

TABLE 5-continued

Potentiation of Etoposide and Compound 1
calculated as GI50 (127 cell lines panel)

| | | μM (±Compound 1) | | Combination | Effect |
|---|---|---|---|---|---|
| Origin | Cell line | Etoposide | +300 nM | Average | +300 nM |
| lung | NCI-H1882 | 0.06 | 0.02 | −0.03 | 0.23 |
| lung | NCI-H1915 | 1.19 | 0.14 | −0.62 | 0.07 |
| lung | NCI-H196 | 1.55 | 0.04 | 0.14 | 0.47 |
| lung | NCI-H1975 | 0.27 | 0.03 | −0.49 | 0.13 |
| lung | NCI-H2030 | 0.45 | 0.02 | −0.29 | 0.34 |
| lung | NCI-H2073 | 2.10 | 0.54 | −0.10 | 0.24 |
| lung | NCI-H2081 | 0.09 | 0.01 | −0.24 | 0.13 |
| lung | NCI-H2085 | 3.15 | 0.01 | −0.28 | 0.41 |
| lung | NCI-H211 | 0.14 | 0.04 | −0.19 | 0.14 |
| lung | NCI-H2110 | 0.21 | 0.02 | −0.68 | 0.07 |
| lung | NCI-H2122 | 0.33 | 0.04 | −0.59 | 0.05 |
| lung | NCI-H2126 | 0.27 | 0.02 | −0.66 | 0.21 |
| lung | NCI-H2141 | 0.51 | 0.13 | −0.16 | 0.13 |
| lung | NCI-H2170 | 1.17 | 0.13 | −0.58 | 0.17 |
| lung | NCI-H2172 | 7.92 | 1.82 | −0.09 | 0.13 |
| lung | NCI-H2196 | 0.80 | 0.09 | −0.13 | 0.29 |
| lung | LUDLU-1 | 1.09 | 0.08 | −0.56 | 0.19 |
| lung | MS-1 | 0.25 | 0.06 | −0.20 | 0.08 |
| lung | NCI-H226 | 0.19 | 0.01 | −0.19 | 0.23 |
| lung | NCI-H2286 | 0.22 | 0.04 | −0.65 | 0.03 |
| lung | NCI-H2291 | 0.13 | 0.06 | 0.13 | 0.34 |
| lung | NCI-H23 | 0.16 | 0.02 | −0.33 | 0.15 |
| lung | NCI-H2342 | 0.52 | 0.19 | −0.10 | 0.03 |
| lung | NCI-H2347 | 0.40 | 0.03 | −0.12 | 0.27 |
| lung | NCI-H2405 | 2.03 | 0.47 | −0.07 | 0.21 |
| lung | NCI-H446 | 0.20 | 0.01 | −0.10 | 0.33 |
| colon | NCI-H508 | 0.98 | 0.16 | −0.20 | 0.26 |
| lung | NCI-H520 | 1.56 | 0.11 | −0.08 | 0.35 |
| lung | NCI-H522 | 0.67 | 0.15 | −0.06 | 0.20 |
| lung | NCI-H524 | 0.29 | 0.03 | −0.62 | 0.13 |
| lung | NCI-H596 | 0.82 | 0.12 | 0.05 | 0.28 |
| lung | NCI-H647 | 0.07 | 0.01 | −0.27 | 0.32 |
| lung | NCI-H661 | 0.23 | 0.04 | −0.03 | 0.37 |
| lung | NCI-H69 | 0.53 | 0.03 | −0.76 | 0.11 |
| lung | LUDLU-1 | 1.09 | 0.08 | −0.56 | 0.19 |
| lung | MS-1 | 0.25 | 0.06 | −0.20 | 0.08 |
| lung | NCI-H774 | 1.43 | 0.34 | −0.19 | 0.26 |
| lung | NCI-H841 | 0.23 | 0.04 | −0.20 | 0.20 |
| lung | NCIH292 | 0.40 | 0.02 | −0.18 | 0.28 |
| lung | NCIH358M | 0.30 | 0.01 | −0.24 | 0.26 |
| lung | NCIH460 | 0.05 | 0.01 | −0.19 | 0.33 |
| lung | NCIH82 | 0.35 | 0.03 | −0.23 | 0.28 |
| lung | NGP | 0.11 | 0.01 | −0.68 | 0.04 |
| lung | PC-9 | 1.41 | 0.13 | −0.94 | 0.04 |
| colon | RKO | 0.68 | 0.11 | −0.45 | 0.05 |
| lung | SCLC-21h | 0.80 | 0.18 | −0.25 | 0.09 |
| lung | SHP-77 | 2.55 | 0.43 | −0.17 | 0.13 |
| colon | SK-CO-1 | 0.31 | 0.05 | −0.26 | 0.26 |
| lung | SK-MES-1 | 0.59 | 0.02 | −0.60 | 0.25 |
| colon | SNU-C1 | >10 | 4.50 | −0.17 | 0.01 |
| lung | SW 900 | 0.42 | 0.04 | −0.16 | 0.23 |
| colon | SW1116 | 0.89 | 0.26 | −0.10 | 0.12 |
| lung | LUDLU-1 | 1.09 | 0.08 | −0.56 | 0.19 |
| lung | MS-1 | 0.25 | 0.06 | −0.20 | 0.08 |
| colon | SW1417 | 2.16 | 0.24 | −0.14 | 0.26 |
| colon | SW48 | 0.04 | <0.002 | −1.02 | 0.15 |
| colon | SW620 | 0.12 | 0.01 | −0.61 | 0.21 |
| colon | SW837 | 0.79 | 0.10 | −0.55 | 0.05 |
| colon | SW948 | 2.35 | 0.20 | −0.81 | 0.08 |
| lung | T3M-11 | 0.16 | 0.01 | −0.27 | 0.32 |
| lung | T3M-12 | 0.40 | 0.17 | −0.17 | 0.02 |
| colon | T84 | 3.04 | 1.10 | −0.23 | −0.03 |

Example 8

Phase Ib: Subjects will receive Compound 1 at the assigned dose level. On Day 1 of each cycle, after oral intake of Compound 1, cisplatin will be administered first, followed by etoposide. In all instances Compound 1 should be administered approximately 1.5 hours before chemotherapy. On Days 2 and 3 of each cycle, Compound 1 should be taken orally QD preferably in the morning. The dose of Compound 1 will be modified according to the dose escalation rules described in this protocol.

Cisplatin and etoposide will be given according to the local guidelines. Most commonly, cisplatin is administered at 75 mg/m$^2$ over a 60-minute iv infusion on Day 1, followed by etoposide administered at 100 mg/m$^2$ over a 60-minute iv infusion. On Days 2 and 3 of each cycle, etoposide can be given either as an iv infusion or orally according to the local guidelines.

Phase II: Subjects will be randomized to receive cisplatin and etoposide in combination with placebo or Compound 1 at the RP2D identified in the Phase Ib part of the trial. On Day 1 of each cycle, after oral intake of Compound 1/placebo, cisplatin will be administered first, followed by etoposide. In all instances Compound 1 should be administered approximately 1.5 hours before chemotherapy. On Days 2 and 3 of each cycle, Compound 1 should be taken orally QD preferably in the morning. Cisplatin and etoposide will be given according to the local guidelines. Most commonly, cisplatin is administered at 75 mg/m2 over a 60-minute iv infusion on Day 1 followed by etoposide administered at 100 mg/m2 over a 60-minute iv infusion. On Days 2 and 3 of each cycle, etoposide can be given either as an intravenous infusion or orally according to the local guidelines.

We claim:
1. A method of treating lung cancer or a histological subtype thereof in a patient in need thereof, comprising administering to said patient Compound 1, or a pharmaceutically acceptable salt thereof:

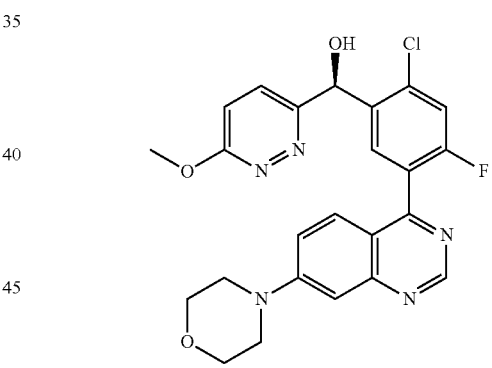

in combination with etoposide and a platin; wherein the method consists of partially or completely alleviating, inhibiting, ameliorating, and/or relieving the lung cancer or histological subtype thereof, or halting its progression.

2. The method according to claim 1, wherein Compound 1 or a pharmaceutically acceptable salt thereof is administered with both etoposide and cisplatin.

3. The method according to claim 1, further comprising the step of administering to the patient radiation therapy.

4. The method according to claim 1, wherein Compound 1 or a pharmaceutically acceptable salt thereof is administered in an amount of about 1 to about 800 mg.

5. The method according to claim 4, wherein Compound 1 or a pharmaceutically acceptable salt thereof is administered in an amount of about 10 to about 800 mg.

6. The method according to claim 1, wherein the etoposide is administered intravenously in an amount of about 100 mg/m$^2$.

7. The method according to claim 6, wherein the etoposide is administered via intravenous infusion over about 1 hour.

8. The method according to claim 2, wherein the cisplatin is administered intravenously in an amount of about 75 mg/m$^2$.

9. The method according to claim 8, wherein the cisplatin is administered via intravenous infusion over about 1 hour.

10. The method according to claim 1, wherein compound 1 acts synergistically in combination with etoposide, wherein etoposide induced myelo- and lymphoid reductions are not further increased by Compound 1.

11. The method according to claim 1, wherein the lung cancer is not b DNA-PK deficient and Compound 1 inhibits repair of DNA double strand breaks via inhibition of DNA-PK.

* * * * *